(12) United States Patent
Zenz-Olson

(10) Patent No.: US 10,258,459 B2
(45) Date of Patent: Apr. 16, 2019

(54) MEDICAL IMPLANT DELIVERY SYSTEM AND RELATED METHODS

(71) Applicant: Rotation Medical, Inc., Plymouth, MN (US)

(72) Inventor: Nathaniel Zenz-Olson, Blaine, MN (US)

(73) Assignee: Rotation Medical, Inc., Plymouth, MN (US)

( * ) Notice: Subject to any disclaimer, the term of this patent is extended or adjusted under 35 U.S.C. 154(b) by 155 days.

(21) Appl. No.: 14/707,509

(22) Filed: May 8, 2015

(65) Prior Publication Data

US 2015/0320543 A1  Nov. 12, 2015

Related U.S. Application Data

(60) Provisional application No. 61/991,001, filed on May 9, 2014.

(51) Int. Cl.
    *A61F 2/00* (2006.01)
    *A61F 2/08* (2006.01)
    *A61B 17/00* (2006.01)

(52) U.S. Cl.
    CPC ...... *A61F 2/0805* (2013.01); *A61B 17/00234* (2013.01); *A61F 2/0063* (2013.01); *A61F 2/08* (2013.01); *A61F 2002/0072* (2013.01)

(58) Field of Classification Search
    CPC .. A61F 2/0805; A61F 2002/0072; A61F 2/92; A61F 2/962; A61F 2/966; A61F 2/97; A61F 2002/9522; A61F 2002/9583
    See application file for complete search history.

(56) References Cited

U.S. PATENT DOCUMENTS

| 511,238 A | 12/1893 | Hieatzman |
|---|---|---|
| 765,793 A | 7/1904 | Ruckel |
| 1,728,316 A | 6/1928 | Von Wachenfeldt |
| 1,868,100 A | 1/1929 | Goodstein |

(Continued)

FOREIGN PATENT DOCUMENTS

| CA | 2390508 A1 | 5/2001 |
|---|---|---|
| EP | 0142225 A1 | 5/1985 |

(Continued)

OTHER PUBLICATIONS

Alexander et al., "Ligament and tendon repair with an absorbable polymer-coated carbon fiber stent", Bulletin of the Hospital for Joint Diseases Orthopaedic Institute, 46(2): 155-173, Fall 1986.

(Continued)

*Primary Examiner* — Andrew M Iwamaye
(74) *Attorney, Agent, or Firm* — Seager, Tufte & Wickhem LLP.

(57) ABSTRACT

An implant assembly for introducing and positioning implants within patients may comprise an implant device, an implant, and a sheath. The implant device may include a head, an upper beam, a lower beam, and an implant positioning component. The implant may be disposed between the upper beam and the lower beam and may include a first face engaged with the upper beam and a second face engaged with the lower beam. Additionally, the implant may be at least partially disposed around the implant positioning component. The sheath may be disposed around the implant positioning device and the implant.

30 Claims, 36 Drawing Sheets

(56) References Cited

U.S. PATENT DOCUMENTS

| | | |
|---|---|---|
| 1,855,546 A | 4/1931 | File |
| 1,910,688 A | 8/1931 | Goodstein |
| 1,940,351 A | 3/1933 | Howard |
| 2,034,785 A | 7/1935 | Charles |
| 2,075,508 A | 3/1937 | Davidson |
| 2,131,321 A | 9/1938 | Wilber |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | Place |
| 2,316,297 A | 4/1943 | Southerland et al. |
| 2,421,193 A | 5/1947 | Gardner |
| 2,571,813 A | 10/1951 | Austin |
| 2,630,316 A | 3/1953 | Foster |
| 2,684,070 A | 7/1954 | Kelsey |
| 2,744,251 A | 5/1956 | Leonhard |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Abraham |
| 3,077,812 A | 2/1963 | Gerhard |
| 3,103,666 A | 9/1963 | Bone |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner, Jr. |
| 3,717,294 A | 2/1973 | Green |
| 3,757,629 A | 9/1973 | Schneider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy |
| 4,570,623 A | 2/1986 | Ellison et al. |
| 4,595,007 A | 6/1986 | Mericle |
| 4,624,254 A | 11/1986 | McGarry et al. |
| 4,627,437 A | 12/1986 | Bedi et al. |
| 4,632,100 A | 12/1986 | Somers et al. |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,740,207 A * | 4/1988 | Kreamer .............. A61F 2/92 606/108 |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gatturna |
| 4,976,715 A | 12/1990 | Bays et al. |
| 4,994,073 A | 2/1991 | Green |
| 4,997,436 A | 3/1991 | Oberlander |
| 5,002,536 A | 3/1991 | Thompson et al. |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach |
| 5,122,155 A | 6/1992 | Eberbach |
| 5,123,913 A | 6/1992 | Wilk et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | McKinney |
| 5,171,259 A | 12/1992 | Inoue |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,203,787 A | 4/1993 | Noblitt et al. |
| 5,217,472 A | 6/1993 | Green et al. |
| 5,224,946 A | 7/1993 | Hayhurst et al. |
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,282,829 A | 2/1994 | Hermes |
| 5,289,963 A | 3/1994 | McGarry et al. |
| 5,290,217 A | 3/1994 | Campos |
| 5,304,187 A | 4/1994 | Green et al. |
| 5,333,624 A | 8/1994 | Tovey |
| 5,342,396 A | 8/1994 | Cook |
| 5,350,400 A | 9/1994 | Esposito et al. |
| 5,352,229 A | 10/1994 | Goble et al. |
| 5,354,292 A | 10/1994 | Braeuer et al. |
| 5,364,408 A | 11/1994 | Gordon |
| 5,366,460 A | 11/1994 | Eberbach |
| 5,370,650 A | 12/1994 | Tovey et al. |
| 5,372,604 A | 12/1994 | Trott |
| 5,380,334 A | 1/1995 | Torrie et al. |
| 5,383,477 A | 1/1995 | DeMatteis |
| 5,397,332 A | 3/1995 | Kammerer et al. |
| 5,403,326 A | 4/1995 | Harrison et al. |
| 5,405,360 A | 4/1995 | Tovey |
| 5,411,522 A | 5/1995 | Trott |
| 5,411,523 A | 5/1995 | Goble |
| 5,417,691 A | 5/1995 | Hayhurst |
| 5,417,712 A | 5/1995 | Whittaker et al. |
| 5,425,490 A | 6/1995 | Goble et al. |
| 5,441,502 A | 8/1995 | Bartlett |
| 5,441,508 A | 8/1995 | Gazielly et al. |
| 5,456,720 A | 10/1995 | Schultz et al. |
| 5,464,403 A | 11/1995 | Kieturakis et al. |
| 5,478,354 A | 12/1995 | Tovey et al. |
| 5,482,864 A | 1/1996 | Knobel |
| 5,486,197 A | 1/1996 | Le et al. |
| 5,497,933 A | 3/1996 | DeFonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |

(56) References Cited

U.S. PATENT DOCUMENTS

| | | |
|---|---|---|
| 5,520,700 A | 5/1996 | Beyar et al. |
| 5,522,817 A | 6/1996 | Sander et al. |
| 5,545,180 A | 8/1996 | Le et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,618,314 A | 4/1997 | Harwin et al. |
| 5,622,257 A | 4/1997 | Deschenes et al. |
| 5,622,527 A | 4/1997 | Watterson et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,782,864 A | 7/1998 | Lizardi |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,824,055 A * | 10/1998 | Spiridigliozzi ......... A61F 2/954 606/195 |
| 5,830,221 A | 11/1998 | Stein et al. |
| 5,836,961 A | 11/1998 | Kieturakis et al. |
| 5,868,762 A | 2/1999 | Cragg et al. |
| 5,873,891 A | 2/1999 | Sohn |
| 5,885,258 A | 3/1999 | Sachdeva et al. |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | DiPoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A | 12/1999 | Person et al. |
| 6,063,088 A | 5/2000 | Winslow |
| 6,099,518 A | 8/2000 | Adams et al. |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,536 B1 | 11/2001 | Rosengart et al. |
| 6,322,563 B1 | 11/2001 | Cummings et al. |
| 6,325,805 B1 | 12/2001 | Ogilvie et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 | 7/2002 | Knodel et al. |
| 6,436,110 B2 | 8/2002 | Bowman et al. |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,289 B1 | 7/2003 | Bojarski et al. |
| 6,620,185 B1 | 9/2003 | Harvie et al. |
| 6,629,988 B2 | 10/2003 | Weadock |
| 6,638,297 B1 | 10/2003 | Huitema |
| 6,639,365 B2 | 10/2003 | Pruett |
| 6,648,893 B2 | 11/2003 | Dudasik |
| 6,666,672 B1 | 12/2003 | Steffens |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,746,500 B1 | 6/2004 | Park et al. |
| 6,764,500 B1 | 7/2004 | Muijs Van De Moer et al. |
| 6,770,073 B2 | 8/2004 | McDevitt |
| 6,779,701 B2 | 8/2004 | Bailly et al. |
| 6,800,081 B2 | 10/2004 | Parodi |
| 6,835,206 B2 | 12/2004 | Jackson |
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,939,365 B1 | 9/2005 | Fogarty et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins |
| 7,021,316 B2 | 4/2006 | Leigoff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Loshakove et al. |
| 7,083,638 B2 | 8/2006 | Foerster |
| 7,087,064 B1 | 8/2006 | Hyde |
| 7,112,214 B2 | 9/2006 | Peterson et al. |
| 7,118,581 B2 | 10/2006 | Friden |
| 7,122,214 B2 | 10/2006 | Xie |
| 7,144,403 B2 | 12/2006 | Booth |
| 7,144,413 B2 | 12/2006 | Wilford et al. |
| 7,144,414 B2 | 12/2006 | Harvie et al. |
| 7,150,750 B2 | 12/2006 | Damarati |
| 7,153,314 B2 | 12/2006 | Laufer et al. |
| 7,160,314 B2 | 1/2007 | Sgro et al. |
| 7,160,326 B2 | 1/2007 | Ball |
| 7,163,536 B2 | 1/2007 | Godara |
| 7,163,551 B2 | 1/2007 | Anthony et al. |
| 7,163,563 B2 | 1/2007 | Schwartz et al. |
| 7,169,157 B2 | 1/2007 | Kayan |
| 7,188,581 B1 | 3/2007 | Davis et al. |
| 7,189,251 B2 | 3/2007 | Kay |
| 7,201,754 B2 | 4/2007 | Stewart et al. |
| 7,214,232 B2 | 5/2007 | Bowman et al. |
| 7,226,469 B2 | 6/2007 | Benavitz et al. |
| 7,229,452 B2 | 6/2007 | Kayan |
| 7,247,164 B1 | 7/2007 | Ritchart et al. |
| 7,303,577 B1 | 12/2007 | Dean |
| 7,306,337 B2 | 12/2007 | Ji et al. |
| 7,309,337 B2 | 12/2007 | Colleran et al. |
| 7,320,692 B1 | 1/2008 | Bender et al. |

(56) References Cited

U.S. PATENT DOCUMENTS

| | | |
|---|---|---|
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |
| 7,460,913 B2 | 12/2008 | Kuzma et al. |
| 7,463,933 B2 | 12/2008 | Wahlstrom et al. |
| 7,465,308 B2 | 12/2008 | Sikora et al. |
| 7,481,832 B1 | 1/2009 | Meridew et al. |
| 7,485,124 B2 | 2/2009 | Kuhns et al. |
| 7,497,854 B2 | 3/2009 | Gill et al. |
| 7,500,972 B2 | 3/2009 | Voegele et al. |
| 7,500,980 B2 | 3/2009 | Gill et al. |
| 7,500,983 B1 | 3/2009 | Kaiser et al. |
| 7,503,474 B2 | 3/2009 | Hillstead et al. |
| 7,506,791 B2 | 3/2009 | Omaits et al. |
| 7,559,941 B2 | 7/2009 | Zannis et al. |
| 7,572,276 B2 | 8/2009 | Lim et al. |
| 7,585,311 B2 | 9/2009 | Green et al. |
| 7,766,208 B2 | 8/2010 | Epperly et al. |
| 7,771,440 B2 | 8/2010 | Ortiz et al. |
| 7,776,057 B2 | 8/2010 | Laufer et al. |
| 7,780,685 B2 | 8/2010 | Hunt et al. |
| 7,785,255 B2 | 8/2010 | Malkani |
| 7,807,192 B2 | 10/2010 | Li et al. |
| 7,819,880 B2 | 10/2010 | Zannis et al. |
| 7,846,171 B2 | 12/2010 | Kullas et al. |
| 7,867,222 B1 | 1/2011 | Tilton, Jr. et al. |
| 7,918,879 B2 | 4/2011 | Yeung et al. |
| 8,114,101 B2 | 2/2012 | Criscuolo et al. |
| 8,197,837 B2 | 6/2012 | Jamiolkowski et al. |
| 8,585,773 B1 | 11/2013 | Kucklick |
| 9,878,141 B2 | 1/2018 | Kucklick |
| 2002/0077687 A1 | 6/2002 | Ahn |
| 2002/0082588 A1 | 6/2002 | McMahon et al. |
| 2002/0090725 A1 | 7/2002 | Simpson et al. |
| 2002/0123767 A1 | 9/2002 | Prestel |
| 2002/0165559 A1 | 11/2002 | Grant et al. |
| 2003/0073979 A1 | 4/2003 | Naimark et al. |
| 2003/0125748 A1 | 7/2003 | Li et al. |
| 2003/0212456 A1 | 11/2003 | Lipchitz et al. |
| 2004/0059416 A1 | 3/2004 | Murray et al. |
| 2004/0138705 A1 | 7/2004 | Heino et al. |
| 2004/0167519 A1 | 8/2004 | Weiner et al. |
| 2005/0015021 A1 | 1/2005 | Shiber |
| 2005/0049618 A1 | 3/2005 | Masuda et al. |
| 2005/0051597 A1 | 3/2005 | Toledano |
| 2005/0059996 A1 | 3/2005 | Bauman et al. |
| 2005/0060033 A1 | 3/2005 | Vacanti et al. |
| 2005/0107807 A1 | 5/2005 | Nakao |
| 2005/0113736 A1 | 5/2005 | Orr et al. |
| 2005/0171569 A1 | 8/2005 | Girard et al. |
| 2005/0187576 A1 | 8/2005 | Whitman et al. |
| 2005/0240222 A1 | 10/2005 | Shipp |
| 2005/0274768 A1 | 12/2005 | Cummins et al. |
| 2006/0074423 A1 | 4/2006 | Alleyne et al. |
| 2006/0178743 A1 | 8/2006 | Carter |
| 2006/0235442 A1 | 10/2006 | Huitema |
| 2006/0293760 A1 | 12/2006 | Dedeyne |
| 2007/0078477 A1 | 4/2007 | Heneveld et al. |
| 2007/0083236 A1 | 4/2007 | Sikora et al. |
| 2007/0112361 A1 | 5/2007 | Schonholz et al. |
| 2007/0179531 A1 | 8/2007 | Thornes |
| 2007/0185506 A1 | 8/2007 | Jackson |
| 2007/0190108 A1 | 8/2007 | Datta et al. |
| 2007/0219558 A1 | 9/2007 | Deutsch |
| 2007/0270804 A1 | 11/2007 | Chudik |
| 2007/0288023 A1 | 12/2007 | Pellegrino et al. |
| 2008/0027470 A1 | 1/2008 | Hart et al. |
| 2008/0051888 A1 | 2/2008 | Ratcliffe et al. |
| 2008/0065153 A1 | 3/2008 | Allard et al. |
| 2008/0090936 A1 | 4/2008 | Fujimura et al. |
| 2008/0125869 A1 | 5/2008 | Paz et al. |
| 2008/0135600 A1 | 6/2008 | Hiranuma et al. |
| 2008/0173691 A1 | 7/2008 | Mas et al. |
| 2008/0188874 A1 | 8/2008 | Henderson |
| 2008/0188936 A1 | 8/2008 | Ball et al. |
| 2008/0195119 A1 | 8/2008 | Ferree |
| 2008/0200949 A1 | 8/2008 | Hiles et al. |
| 2008/0241213 A1 | 10/2008 | Chun et al. |
| 2008/0272173 A1 | 11/2008 | Coleman et al. |
| 2008/0306408 A1 | 12/2008 | Lo |
| 2009/0001122 A1 | 1/2009 | Prommersberger et al. |
| 2009/0012521 A1 | 1/2009 | Axelson et al. |
| 2009/0030434 A1 | 1/2009 | Paz et al. |
| 2009/0069806 A1 | 3/2009 | De La et al. |
| 2009/0076541 A1 | 3/2009 | Chin et al. |
| 2009/0105535 A1 | 4/2009 | Green et al. |
| 2009/0112085 A1 | 4/2009 | Eby |
| 2009/0134198 A1 | 5/2009 | Knodel et al. |
| 2009/0156986 A1 | 6/2009 | Trenhaile |
| 2009/0156997 A1 | 6/2009 | Trenhaile |
| 2009/0182245 A1 | 7/2009 | Zambelli |
| 2009/0242609 A1 | 10/2009 | Kanner |
| 2010/0145367 A1 | 6/2010 | Ratcliffe |
| 2010/0147922 A1 | 6/2010 | Olson |
| 2010/0163598 A1 | 7/2010 | Belzer |
| 2010/0191332 A1 | 7/2010 | Euteneuer et al. |
| 2010/0241227 A1 | 9/2010 | Euteneuer et al. |
| 2010/0249801 A1 | 9/2010 | Sengun et al. |
| 2010/0256675 A1 | 10/2010 | Romans |
| 2010/0274278 A1 | 10/2010 | Fleenor |
| 2010/0292715 A1 | 11/2010 | Nering et al. |
| 2010/0292791 A1 | 11/2010 | Lu et al. |
| 2010/0312250 A1 | 12/2010 | Euteneuer et al. |
| 2010/0312275 A1 | 12/2010 | Euteneuer et al. |
| 2010/0312357 A1* | 12/2010 | Levin .................. A61B 17/064 623/23.72 |
| 2010/0327042 A1 | 12/2010 | Amid et al. |
| 2011/0000950 A1 | 1/2011 | Euteneuer et al. |
| 2011/0004221 A1 | 1/2011 | Euteneuer et al. |
| 2011/0011917 A1 | 1/2011 | Loulmet |
| 2011/0034942 A1 | 2/2011 | Levin et al. |
| 2011/0040310 A1 | 2/2011 | Levin et al. |
| 2011/0040311 A1 | 2/2011 | Levin et al. |
| 2011/0066166 A1 | 3/2011 | Levin et al. |
| 2011/0106154 A1 | 5/2011 | Dimatteo et al. |
| 2011/0114700 A1 | 5/2011 | Baxter, III et al. |
| 2011/0224702 A1 | 9/2011 | Van Kampen et al. |
| 2011/0264149 A1 | 10/2011 | Pappalardo et al. |
| 2012/0100200 A1 | 4/2012 | Belcheva et al. |
| 2012/0160893 A1 | 6/2012 | Harris et al. |
| 2012/0193391 A1 | 8/2012 | Michler et al. |
| 2012/0209401 A1 | 8/2012 | Euteneuer et al. |
| 2012/0211543 A1 | 8/2012 | Euteneuer |
| 2012/0248171 A1 | 10/2012 | Bailly et al. |
| 2012/0316608 A1 | 12/2012 | Foley |
| 2013/0018395 A1* | 1/2013 | Friedlander ........... A61F 2/0063 606/151 |
| 2013/0035704 A1* | 2/2013 | Dudai .................. A61F 2/0063 606/151 |
| 2013/0110156 A1 | 5/2013 | Nakayama et al. |
| 2013/0153627 A1 | 6/2013 | Euteneuer et al. |
| 2013/0153628 A1 | 6/2013 | Euteneuer |
| 2013/0158554 A1 | 6/2013 | Euteneuer et al. |
| 2013/0158587 A1 | 6/2013 | Euteneuer et al. |
| 2013/0158661 A1 | 6/2013 | Euteneuer et al. |
| 2013/0172920 A1 | 7/2013 | Euteneuer et al. |
| 2013/0172997 A1 | 7/2013 | Euteneuer et al. |
| 2013/0184716 A1 | 7/2013 | Euteneuer et al. |
| 2013/0240598 A1 | 9/2013 | Euteneuer et al. |
| 2013/0245627 A1 | 9/2013 | Euteneuer et al. |
| 2013/0245682 A1 | 9/2013 | Euteneuer et al. |
| 2013/0245683 A1 | 9/2013 | Euteneuer et al. |
| 2013/0245706 A1 | 9/2013 | Euteneuer et al. |
| 2013/0245707 A1 | 9/2013 | Euteneuer et al. |
| 2013/0245762 A1 | 9/2013 | Van Kampen et al. |

(56) References Cited

U.S. PATENT DOCUMENTS

| | | | |
|---|---|---|---|
| 2013/0245774 A1 | 9/2013 | Euteneuer et al. | |
| 2014/0114331 A1 | 4/2014 | Levin et al. | |
| 2015/0088169 A1* | 3/2015 | Kelly | A61F 2/0063 606/151 |
| 2016/0256254 A1 | 9/2016 | Kucklick | |
| 2016/0262780 A1 | 9/2016 | Kucklick | |

FOREIGN PATENT DOCUMENTS

| | | | |
|---|---|---|---|
| EP | 0298400 A1 | 1/1989 | |
| EP | 0390613 A1 | 10/1990 | |
| EP | 0543499 A1 | 5/1993 | |
| EP | 0548998 A1 | 6/1993 | |
| EP | 0557963 A1 | 9/1993 | |
| EP | 0589306 A2 | 3/1994 | |
| EP | 0908152 A1 | 4/1999 | |
| EP | 1491157 A1 | 12/2004 | |
| EP | 1559379 A1 | 8/2005 | |
| EP | 2030576 A2 | 3/2009 | |
| GB | 2154688 A | 9/1985 | |
| GB | 2397240 A | 7/2004 | |
| JP | 58188442 A | 11/1983 | |
| JP | 2005506122 A | 3/2005 | |
| JP | 2006515774 A | 6/2006 | |
| WO | 8505025 A1 | 11/1985 | |
| WO | 2001091644 A1 | 6/2001 | |
| WO | 0176456 A2 | 10/2001 | |
| WO | 01091644 A1 | 12/2001 | |
| WO | 0234140 A2 | 5/2002 | |
| WO | 03105670 A2 | 12/2003 | |
| WO | 2004000138 A1 | 12/2003 | |
| WO | 2004093690 A1 | 11/2004 | |
| WO | 2005016389 A2 | 2/2005 | |
| WO | 2006086679 A1 | 8/2006 | |
| WO | 2007014910 A1 | 2/2007 | |
| WO | 2007030676 A2 | 3/2007 | |
| WO | 2007078978 A2 | 7/2007 | |
| WO | 2007082088 A2 | 7/2007 | |
| WO | 2008111073 A2 | 9/2008 | |
| WO | 2008111078 A2 | 9/2008 | |
| WO | 2008139473 A2 | 11/2008 | |
| WO | 2009079211 A1 | 6/2009 | |
| WO | 2009143331 A1 | 11/2009 | |
| WO | 2011095890 A2 | 8/2011 | |
| WO | 2011128903 A2 | 10/2011 | |
| WO | 2018144887 A1 | 8/2018 | |

OTHER PUBLICATIONS

Bahler et. al., "Trabecular bypass stents decrease intraocular pressure in cultured human anterior segments", Am. J. Ophthalmology, 138(6): 988-994, Dec. 2004.

Chamay et al., "Digital contracture deformity after implantation of a silicone prosthesis: Light and electron microscopic study", Journal of Hand Surgery, 3(3): 266-270, May 1978.

D'Ermo et al., "Our results with the operation of ab externo trabeculotomy", Ophthalmologica, 163(5): 347-355, 1971.

France et al., "Biomechanical evaluation of rotator cuff fixation methods", American Journal of Sports Medicine, 17(2): 176-181, Mar. 1989.

Goodship et al., "An assessment of filamentous carbon fibre for the treatment of tendon injury in the horse", Veterinary Record, 106(10): 217-221, Mar. 8, 1980.

Hunter et al., "Flexor-tendon reconstruction in severely damaged hands", Journal of Bone and Joint Surgery Am, 53(5): 829-858, Jul. 1971.

Johnstone et al., "Microsurgery of Schlemm's canal and the human aqueous outflow system", Am J. Ophthalmology, 76(6): 906-917, Dec. 1973.

Kowalsky et al., "Evaluation of suture abrasion against rotator cuff tendon and proximal humerus bone", Arthroscopy: The Journal of Arthroscopic and Related Surgery, 24(3): 329-334, Mar. 2008.

Lee et al., "Aqueous-venous shunt and intraocular pressure: Preliminary report of animal studies", Investigative Ophthalmology, 5(1): 59-64, Feb. 1966.

Mäepea et al., "The pressures in the episcleral veins, Schlemm's canal and the trabecular meshwork in monkeys: Effects of changes in intraocular pressure", Experimental Eye Research, 49(4): 645-663, Oct. 1989.

Nicolle et al., "A silastic tendon prosthesis as an adjunct to flexor tendon grafting: An experimental and clinical evaluation", British Journal of Plastic Surgery, 22(3-4): 224-236, 1969.

Rubin et al., "The use of acellular biologic tissue patches in foot and ankle surgery", Clinics in Podiatric Medicine and Surgery, 22(4): 533-552, Oct. 2005.

Schultz, "Canaloplasty procedure shows promise for open-angle glaucoma in European study", Ocular Surgery News, pp. 34-35, Mar. 1, 2007.

Spiegel et al., "Schlemm's canal implant: A new method to lower intraocular pressure in patients with POAG?", Ophthalmic Surgery and Lasers, 30(6): 492-494, Jun. 1999.

Stetson et al., "Arthroscopic treatment of partial rotator cuff tears", Operative Techniques in Sports Medicine, 12(2): 135-148, Apr. 2004.

Valdez et al., "Repair of digital flexor tendon lacerations in the horse, using carbon fiber implants", Journal of the American Veterinary Medical Association [JAVMA], 177(5): 427-435, Sep. 1, 1980.

Wikipedia: The Free Encyclopedia, "Rotator cuff tear", downloaded from <http://en.wikipedia.org/wiki/Rotator_cuff_tear> on Dec. 6, 2012; 14 pages.

* cited by examiner

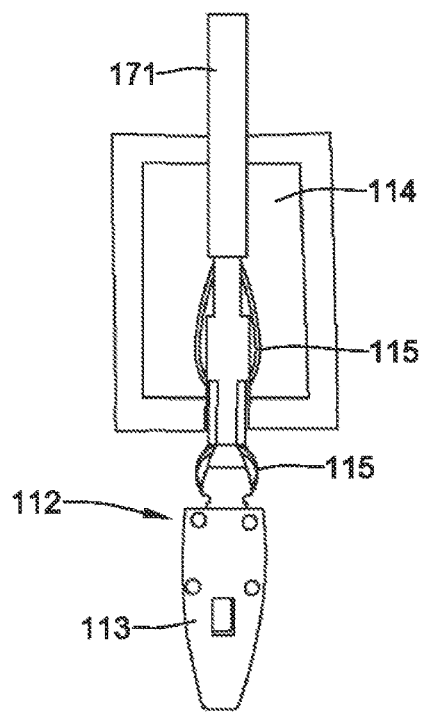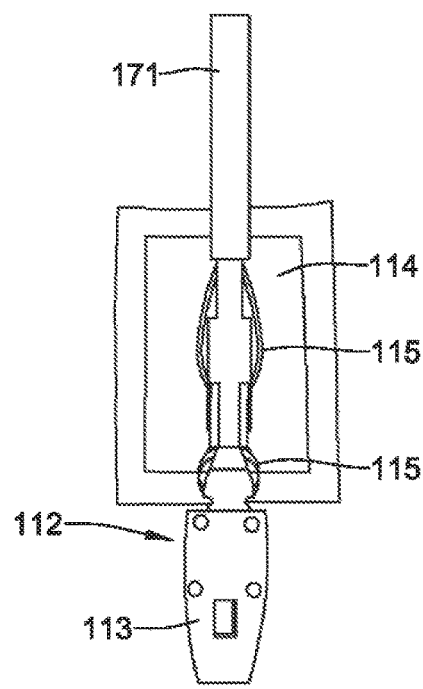
FIG. 12J  FIG. 12K
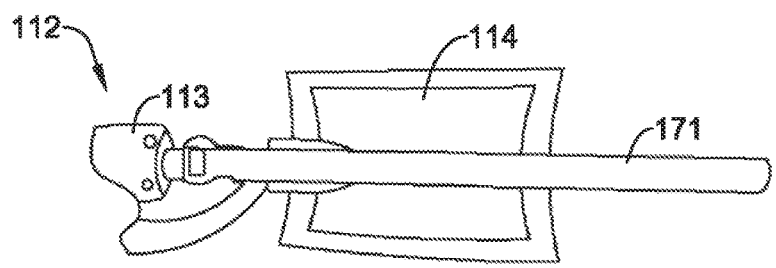
FIG. 12L
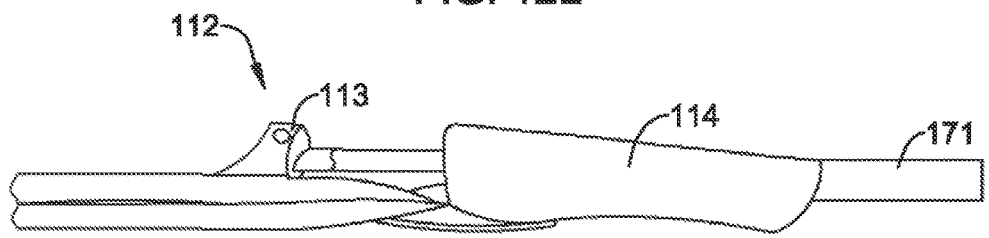
FIG. 12M

MEDICAL IMPLANT DELIVERY SYSTEM AND RELATED METHODS

CROSS-REFERENCE TO RELATED APPLICATION

This application claims priority under 35 U.S.C. § 119 to U.S. Provisional Application Ser. No. 61/991,001, filed May 9, 2014, the entirety of which is incorporated herein by reference.

TECHNICAL FIELD

The present disclosure pertains generally, but not by way of limitation, to medical devices, and methods for manufacturing medical devices. More particularly, the present disclosure pertains to devices for introducing and positioning implants within patients, and methods for manufacturing and using such devices.

BACKGROUND

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. Adequate procedures do not exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. There is an ongoing need to deliver and adequately position medical implants during an arthroscopic procedure in order to treat injuries to the rotator cuff, rotator cuff tendons, or other soft tissue or tendon injuries throughout a body.

BRIEF SUMMARY

The disclosure describes various medical devices and methods for using medical devices to assist in delivering and positioning implants within a body. In a first example, an implant assembly comprises an implant device including a head, an upper beam, a lower beam, and an implant positioning component; an implant, including a first face and a second face, disposed between the upper beam and the lower beam, wherein the first face is engaged with the upper beam, the second face is engaged with the lower beam, and the implant is at least partially disposed around the implant positioning component; and a sheath disposed around the implant positioning device and the implant.

Alternatively or additionally to the above example, in another example, the sheath is retractably disposed around the implant positioning device and the implant.

Alternatively or additionally to the examples above, in another example, the sheath is configured to releasably engage with a delivery device.

Alternatively or additionally to the examples above, in another example, the sheath further comprises an engagement head for engaging with a delivery device.

Alternatively or additionally to the examples above, in another example, the engagement head comprises one or more notches.

Alternatively or additionally to the examples above, in another example, the sheath is configured to engage with an outer tube of the delivery device, and wherein the implant positioning device is configured to engage with an inner tube of the delivery device.

Alternatively or additionally to the examples above, in another example, the one or more notches are configured to releasably engage one or more engagement arms of a delivery device, and wherein each of the engagement arms comprises a latch to engage at least one of the one or more notches.

Alternatively or additionally to the examples above, in another example, the sheath further comprises a guide wire slit.

Alternatively or additionally to the examples above, in another example, the implant positioning component includes an undeployed state and a deployed state.

Alternatively or additionally to the examples above, in another example, in the deployed state, the implant positioning component extends from a central longitudinal axis of the implant device.

Alternatively or additionally to the examples above, in another example, in the deployed state, the implant positioning component applies a force to the implant.

Alternatively or additionally to the examples above, in another example, the implant positioning component comprises a flexible metal, and wherein in the undeployed state, the implant positioning component is in a relatively deformed state and in the deployed state, the implant positioning component is in a relatively undeformed state.

Alternatively or additionally to the examples above, in another example, when the sheath is disposed about the implant positioning component, the sheath biases the implant positioning component to the undeployed state.

Alternatively or additionally to the examples above, in another example, the implant positioning component and the implant move relative to the sheath to transition from the undeployed state to the deployed state.

Alternatively or additionally to the examples above, in another example, the implant is uncovered by the sheath in the deployed state.

Alternatively or additionally to the examples above, in another example, the assembly further comprises an implant assembly loading vessel and a loading tube.

Alternatively or additionally to the examples above, in another example, the loading tube is configured to retain the implant positioning component in an undeployed state.

Alternatively or additionally to the examples above, in another example, the loading tube comprises an implant positioning component engagement slot configured to receive the implant positioning component.

Alternatively or additionally to the examples above, in another example, the assembly comprising wherein the implant positioning component traverses the positioning component engagement slot and at least partially resides in the loading tube.

Alternatively or additionally to the examples above, in another example, one of the upper beam and the lower beam are disposed within the loading tube when the loading tube engages the implant device.

Alternatively or additionally to the examples above, in another example, the implant assembly and the loading tube are configured to engage with the implant loading vessel, and the loading tube is configured to securely engage with the implant loading vessel and the implant assembly is configured to releasably engage with the implant loading vessel.

Alternatively or additionally to the examples above, in another example, the implant loading vessel further includes a channel for the loading tube, the channel including a raised tab, and the loading tube further includes a slot configured to engage with the raised tab to securely engage the loading tube with the implant cartridge loading vessel.

Alternatively or additionally to the examples above, in another example, the assembly comprising wherein the implant cartridge loading vessel comprises one or more sheath head engagement portions configured to engage the sheath head.

Furthermore, another example includes an implant delivery device including an inner tube having a distal end and a proximal end, wherein the inner tube is configured to receive a guidewire; an outer tube with a distal end and a proximal end, wherein the outer tube is at least partially disposed around the inner tube, a handle disposed near the proximal end of the inner tube and the proximal end of the outer tube, wherein the handle is operatively connected to the inner tube and the outer tube; a trigger operatively connected to the handle, wherein movement of the trigger causes the outer tube to move axially relative to the inner tube; and an indicator device operatively connected to the handle, wherein the indicator device provides an indication when a guidewire reaches a predetermined position relative to the implant delivery device.

Alternatively or additionally to the above example, in another example, the indicator device includes an indication when the guide wire contacts the indicator.

Alternatively or additionally to the examples above, in another example, a contact force between the indicator and the guide wire causes the indictor to provide an indication.

Alternatively or additionally to the examples above, in another example, the indicator device includes a visual indicator.

Alternatively or additionally to the examples above, in another example, the indicator device includes an auditory indicator.

Alternatively or additionally to the examples above, in another example, the indicator moves relative to the implant delivery device when the visual indicator provides an indication.

Alternatively or additionally to the examples above, in another example, the device comprising wherein a color of the indicator is different from a color of the delivery device.

Alternatively or additionally to the examples above, in another example, the outer tube further includes one or more attachment arms for engaging an implant device including an implant.

Alternatively or additionally to the examples above, in another example the one or more attachment arms comprise one or more engagement features for engagement with the implant cartridge.

Alternatively or additionally to the examples above, in another example, movement of the trigger causes proximal movement of the outer tube away from the distal end of the inner tube.

Furthermore in another example, an implant assembly comprises an implant device including a head, an upper beam, a lower beam, and one or more implant positioning components; and a loading tube configured to engage the one or more implant positioning components, wherein when engaged, the loading tube retains the one or more implant positioning components in an undeployed state.

Alternatively or additionally to the above example, in another example, the loading tube further includes a slot and wherein in the undeployed state, the implant positioning component traverses the slot and at least a portion of the implant positioning component resides within the loading tube.

Alternatively or additionally to the examples above, in another example, the assembly comprising wherein the slot is a first slot, the implant positioning component is a first implant positioning component, and the loading tube further includes a second slot, and in the undeployed state, a second implant positioning component traverses the second slot and at least a portion of the second implant positioning component resides in the loading tube.

Alternatively or additionally to the examples above, in another example, the assembly comprising wherein the loading tube further includes a tab formed from a cut out portion of a wall of the loading tube and in the undeployed state, a first implant positioning component is disposed such that at least a portion of the implant positioning component is retained in the undeployed state by the tab.

Alternatively or additionally to the examples above, in another example, the tab is a first tab, and the loading tube further includes a second tab, and in the undeployed state a second implant positioning component is disposed such that at least a portion of the second implant positioning component is retained in the undeployed state by the second tab.

Alternatively or additionally to the examples above, in another example, an edge of the cut out portion of the wall includes an angled portion.

Alternatively or additionally to the examples above, in another example, the loading tube further includes an engagement slot for engaging with an implant loading vessel.

The above summary of some examples and embodiments is not intended to describe each disclosed embodiment or every implementation of the present disclosure. The Brief Description of the Drawings, and Detailed Description, which follow, more particularly exemplify these embodiments, but are also intended as exemplary and not limiting.

Figure 1A:
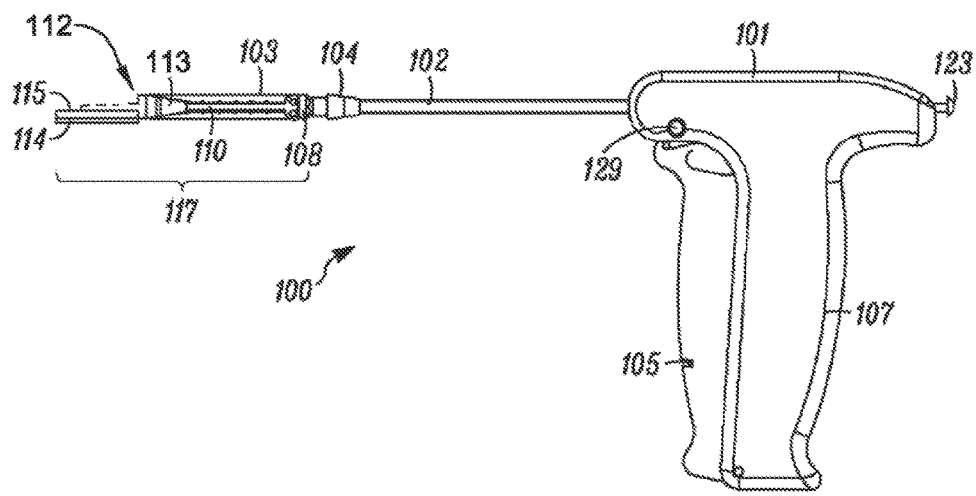
FIGS. 1A-C are perspective views of an exemplary implant delivery system including an actuating handle assembly and implant delivery cartridge assembly, according to an example of the present disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or able to be arranged with each other to form other additional embodiments or to complement and/or enrich the described embodiment(s), as would be understood by one of ordinary skill in the art.

Figure 1B:
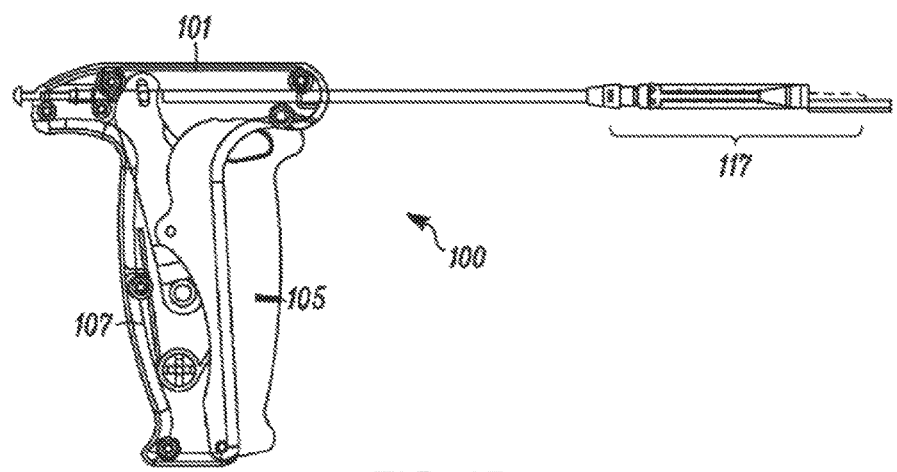
Figure 1C:
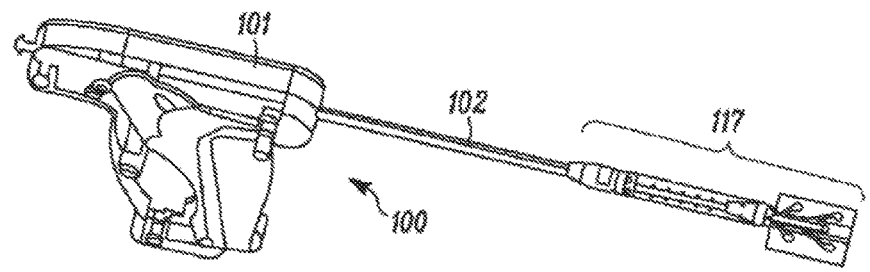

FIGS. 1A-1C provide perspective views of implant delivery system 100. In at least some examples, implant delivery system 100 comprises implant cartridge 117 and delivery device 101. Implant cartridge 117 may releasably attach to delivery device 101, and delivery device 101 may be maneuvered to position implant cartridge 117 at a desired implant location within a patient. Delivery device 101 may be configured to operate with implant cartridge 117 to deploy implant 114 at the desired location.

More specifically, delivery device 101 may include handle 107, trigger 105, outer tube 102, indicator device 123, and safety lock 129. Additionally in some examples, delivery device 101 also includes inner tube 110, which is at least partially disposed within outer tube 102. In at least some examples, outer tube 102 may translate axially with respect to inner tube 110.

Implant cartridge 117 may comprise implant device 112, implant 114, and sheath 103. Implant device 112 may comprise head 113 and implant positioning component 115. Implant 114 may be configured to engage with implant device 112 and implant positioning component 115. Sheath 103 may include engagement head 108 for engaging with outer tube 102. Specifically, engagement head 108 may be configured to engage with connector 104, wherein connector 104 is attached to outer tube 102.

In some examples, implant 114 may comprise one or multiple of a number of different materials without deviating from the spirit and scope of the present disclosure. In some examples, implant 114 may comprise a plurality of fibers. The fibers may be interlinked with one another. When this is the case, implant 114 may comprise a plurality of apertures comprising the interstitial spaces between fibers. Various processes may be used to interlink the fibers with one another. Examples of processes that may be suitable in some applications including weaving, knitting, and braiding. In some embodiments, implant 114 may comprise a laminate including multiple layers of film with each layer of film defining a plurality of micro-machined or formed holes. Implant 114 may also comprise a reconstituted collagen material having a porous structure. Additionally, implant 114 may also comprise a plurality of electro-spun nanofiber filaments forming a composite sheet. Additionally, implant 114 may comprise a synthetic sponge material that defines a plurality of pores. Implant 114 may also comprise a reticulated foam material. Reticulated foam materials that may be suitable in some applications are available from Biomerix Corporation of Fremont, Calif. which identifies these materials using the trademark BIOMERIX BIOMATERIAL™. Implant 114 may be circular, oval, oblong, square, rectangular, or other shape configured to suit the target anatomy.

Figure 2:
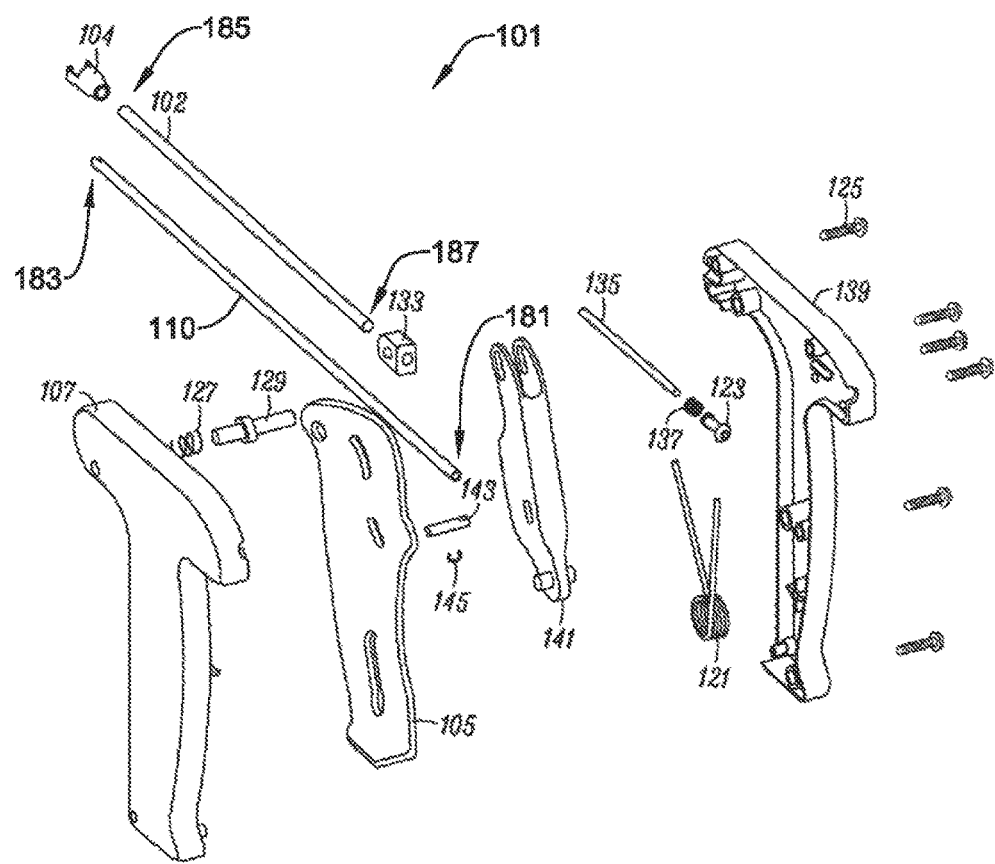
FIG. 2 is an exploded view of an exemplary implant delivery system, according to an example of the present disclosure.

FIG. 2 illustrates an exploded view of exemplary delivery device 101. Inner tube 110 includes proximal end 181 and distal end 183, where proximal end 181 of inner tube 110 is securely connected to handle 107. Clip 145 is attached to inner tube 110 and may resist axial loads applied to inner tube 110, for example when cartridge 117 is attached to outer tube 102 or when sheath 103 is retracted. Inner tube 110 may additionally have an outer diameter that is smaller than an inner diameter of outer tube 102 so that inner tube 110 may be received at least partially within outer tube 102. Additionally, in at least some examples, inner tube 110 has a length greater than that of outer tube 102 such that distal end 183 of inner tube 110 may extend beyond distal end 185 of inner tube 102 when delivery device 101 is fully assembled. Although not shown in FIG. 2, inner tube 110 may also include one or more slots for receiving a guidewire. Outer tube 102 also includes proximal end 187. Distal end 185 of outer tube 102 is securely connected to connector 104, and proximal end 187 of outer tube 102 is securely connected to outer tube linkage connecter 133.

Outer tube linkage connecter 133 is connected to linkage 141, and linkage 141 is connected to trigger 105. The connections between trigger 105, linkage 141, and outer tube linkage connecter 133 are configured such that when trigger 105 is pulled in a proximal direction, e.g. away from distal ends 183 and 185, the force is relayed through the linkage 141 and to the outer tube 102. For example, linkage 141 connects with trigger 105 with axle or pin 143. Spring 121 provides an appropriate resistive force against the user pulling the trigger 105. This applied force causes outer tube 102 to move in a proximal direction relative to inner tube 110, which remains stationary. This proximal movement of outer tube 102 also causes a proximal movement of connector 104 and sheath 103, which is attached to connector 104, as connecter 104 is securely attached to the distal end of outer tube 102. This proximal movement has an effect of uncovering a section of inner tube 110 that had previously been covered by outer tube 102. As seen in FIG. 2, housing 139 may contain such inner components of device 101. Housing 139, and in some examples one or more of the internal components, may be held together by fasteners 125.

Some examples may also include safety lock 129 and spring 127. Safety lock 129 may include a raised portion that protrudes away from a longitudinal axis of safety lock 129. Such a raised portion may be configured to engage with one or more grooves or raised sections (not shown) on an upper section of trigger 105. When assembled, safety lock 129 may be biased toward a first side of delivery device 101 by spring 127 in a locked position. In the locked position, a portion of safety lock 129 extends beyond housing 139 of delivery device 101. When in the locked position, the raised portion of safety lock 129 may engage with the one or more grooves or raised sections of trigger 105 to prevent movement of trigger 105. When a user applies a force to safety lock 129, for example by depressing safety lock 129, sufficient to overcome the biasing force of spring 127, safety lock 129 may move away from the first side of housing 139 and toward a second side of housing 139. When safety lock 129 has moved sufficiently toward the second side of housing 139, the raised portion of safety lock 129 engages with the one or more grooves or raised sections of trigger 105 such that the raised portion no longer prevents movement of trigger 105. This position may be termed an unlocked position. In some examples, a user may need to continually depress safety lock 129 in order to retain safety lock 129 in the unlocked position. However, in other examples, after safety lock 129 has been depressed a threshold amount, safety lock 129 may remain in an unlocked position until trigger 105 has been moved a sufficient amount to release safety lock 129 from the locked position. In some examples, the raised portion of safety lock 129 may engage with the one or more grooves or raised sections of trigger 105 such that after depressing safety lock 129, a user may need to move trigger 105 a small amount in order to retain safety lock in the unlocked position. Such a feature may allow a user to set the device in an unlocked state without continually needing to apply a force to safety lock 129.

In other examples, safety lock 129 may have two separate locked states. For example, when trigger 105 is in a first, un-depressed position, e.g. before a user has moved trigger 105 in a proximal direction, safety lock 129 may be biased in a locked state such that a user may be unable to move trigger 105 in a proximal direction without first transitioning safety lock 129 into an unlocked state. Additionally, after trigger 105 has been moved in a proximal direction a threshold amount, safety lock 129 may again enter a locked state. In such a locked state, safety lock 129 may prevent trigger 105 from being moved in a distal direction. This locked state may prevent accidental movement of trigger 105 after an implant has been deployed. A user may then depress safety lock 129 in order to move safety lock 129 into an unlocked position in order to again allow movement of trigger 105, for example in a distal direction.

Additionally in some examples, device 101 may include indicator 123. Indicator 123 may operate in conjunction with spring 137 and stop 135. For example, spring 137 may bias indicator 123 in a distal position. When pressure is applied to stop 135, stop 135 may impart force on indicator 123. If the pressure applied by stop 135 is greater than the biasing force of spring 137, stop 135 may cause indicator 123 to provide an indication. For instance, the pressure applied by stop 135 may cause indicator 123 to extend beyond housing 139 to provide an indication. In other examples, indicator 123 may make an audible sound, such as a single, intermittent, or continuous audible sound, to provide an indication. In still other examples, indicator 123 may be colored to contrast with housing 139 in order for a user to more easily identify an indication. In some examples, indicator 123 may only provide an indication as long as force is applied to stop 135. For instance, indicator 123 may retract back toward device 101, cease making an audible sound, or make a second audible sound when a force is removed from stop 135.

Indicator 123 may provide an indication of guidewire position. For example, during a procedure, a user may securely fasten a guidewire within a patient at a desired location for placement of implant 114. The user may then advance device 101 over the guidewire, which guides device 101 and implant 114 to the location where the guidewire is fastened. In some examples, a user may not have a clear visual picture of the implant site. Accordingly, a user may rely on indicator 123 to provide an indication when device 101 is in an appropriate position for deployment of implant 114. Indicator 123 may provide such an indication when the guidewire has been advanced far enough into device 101 to contact stopper 135, which would provide a proximal force onto spring 137 and indicator 123 to move indicator 123 proximally. Accordingly, in such examples, a user may need to size the guidewire appropriately such that indicator 123 provides an indication when device 101 is in an appropriate location relative to the desired location. For example, the length of the device from the end of sheath 103 to a first end of stopper 135 may be a fixed length. A guidewire should be sized appropriately (e.g. length-wise) such that when an amount of guidewire longer than the fixed length is advanced into device 101, which would cause the guidewire to contact stopper 135 and, hence, cause indicator 123 to provide an indication, device 101 would be in a desired location for deployment of implant 114. In some examples, system 100 may include such an appropriately sized guidewire. However, in other examples, a user may fashion an appropriately sized guidewire before fastening the guidewire to the patient as the user may be better able to take into account patient specifics, such as the length of the guidewire that needs to be implanted at the desired implant site.

Figure 3:
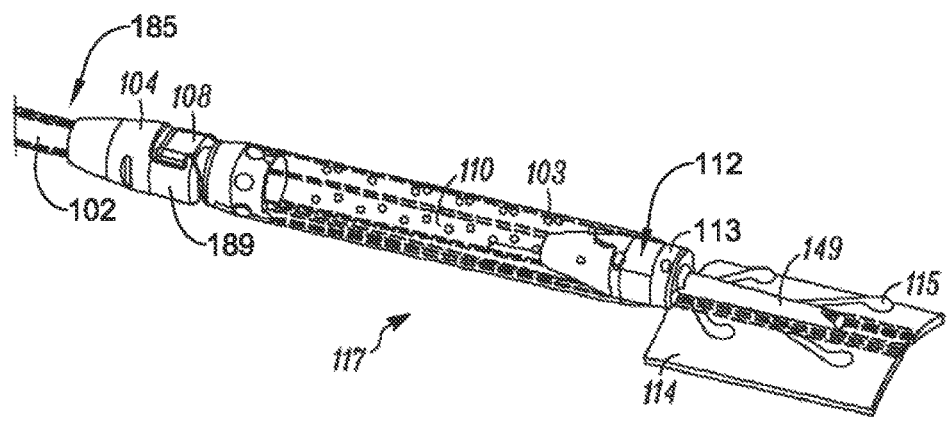
FIG. 3 is a perspective view of an exemplary implant cartridge, according to an example of the present disclosure.

FIG. 3 is an illustration of implant cartridge 117 and distal end 185 of outer tube 102. FIG. 3 also illustrates implant device 112 and implant 114 in a deployed position. At distal end 185 of outer tube 102, connector 104 includes one or more engagement arms 189. Engagement arms 189 may be configured to engage with engagement head 108 of sheath 103. As described previously, inner tube 110 may extend beyond distal end 185 of inner tube 102. Accordingly, when sheath 103 is connected to connector 104, inner tube 110 may extend at least partially into sheath 103, as shown in FIG. 3. In at least some examples, as implant cartridge is attached to outer tube 102, for instance by engaging connector 104 with sheath head 108, inner tube 110 may extend into sheath 103 and engage with implant device 112. For instance, implant device 112 may have inner tube interface component 157 and may receive inner tube 110 into inner tube interface component 157. In some examples, inner tube 110 may engage with implant device 112 before sheath head 108 engages with connector 104 and outer tube 102. In such examples, a user may then know that inner tube 110 has engaged with implant device 112 when sheath head 108 is engaged with connector 104.

Further, in some examples, inner tube 110 may additionally engage with implant device 112. For example, head 113 of implant device 112 may comprise a hollow inner portion into which inner tube 110 fits. When implant device 112 and implant 114 are in an undeployed state, sheath 103 may be disposed around implant device 112 and implant 114. In order to transition implant device 112 and implant 114 from the undeployed state to the deployed state, a user may press trigger 105. As described previously, this may cause movement of outer tube 102 in a proximal direction. When sheath 103 is attached to outer tube 102, for example by engagement between connector 104 and engagement head 108, the movement of outer tube 102 also causes movement of sheath 103 in a proximal direction. Because inner tube 110 remains stationary, implant device 112 and implant 114 also remain stationary. This relative movement has an effect of pulling sheath 103 proximally to uncover implant device 112 and implant 114, resulting in the deployed position illustrated in FIG. 3.

FIG. 3 further illustrates features of implant device 112 and implant 114 from an upper perspective. For example, implant device 112 includes head 113, implant positioning component 115, and upper beam 149. Implant positioning component 115 may include one or more points of contact with implant 114 where implant positioning component 115 may provide force on implant 114. Such force may cause implant 114 to transition from a first undeployed state to a second deployed state. For instance, when implant device 112 and implant 114 are in an undeployed state, implant 114 may be disposed at least partially around upper beam 149 and/or head 113. When sheath 103 is retracted, implant positioning component 115 may cause implant 114 to spread out and/or unfold into the deployed state, as shown in FIG. 3.

Figure 4:
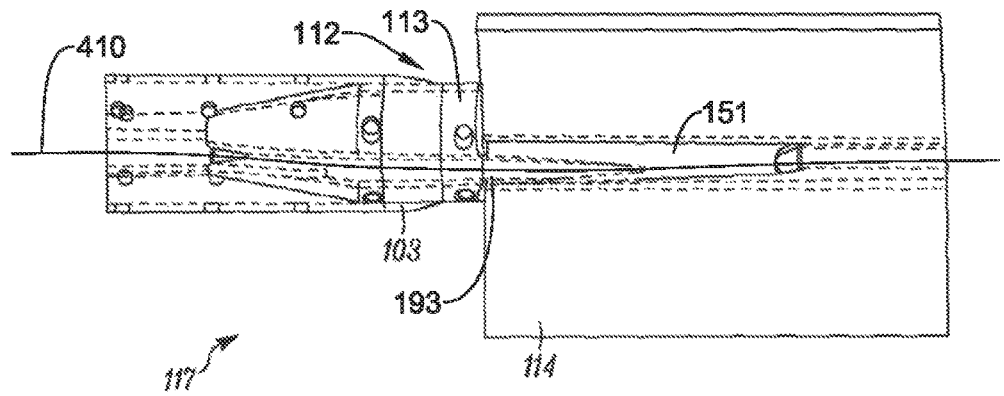
FIG. 4 is a perspective view of an implant device and implant, according to an example of the present disclosure.

FIG. 4 illustrates implant device 112 and implant 114 from a lower perspective. In some examples, implant device 112 additionally includes lower beam 151. In such examples, implant 114 may be disposed between upper beam 149 and lower beam 151 such that a first face of implant 114 is engaged with upper beam 149 and a second face of implant 114 is engaged with lower beam 151. In some examples, a portion of lower beam 151 may include a guidewire groove 193. Additionally in some examples, guidewire groove 193 may also extend to at least a portion of head 113 of implant device 112. Guidewire groove 193 may provide a path for advancing guidewire 410 through device 101. For instance, a user may advance guidewire 410 into a distal end of sheath 103, positioning guidewire 410 in alignment with guidewire groove 193. Guidewire groove 193 may then steer guidewire 410 into the lumen of inner tube 110, where the guidewire may be advanced to stopper 135. In at least some examples, guidewire groove 193 may steer guidewire 410 through engagement head 108 and then into the lumen of inner tube 110. In some examples, guidewire 410 may pass into inner tube 110 through the distal end 183. In other examples, inner tube 110 may have a slit near distal end 183 through which guidewire 410 may enter inner tube 110. Additionally, in some examples, sheath 103 may include sheath slit 159 (shown in FIGS. 6 and 11S), which may allow for easier manipulation of guidewire 410 or device 101 while advancing device 101 along guidewire 410.

Figure 5A:
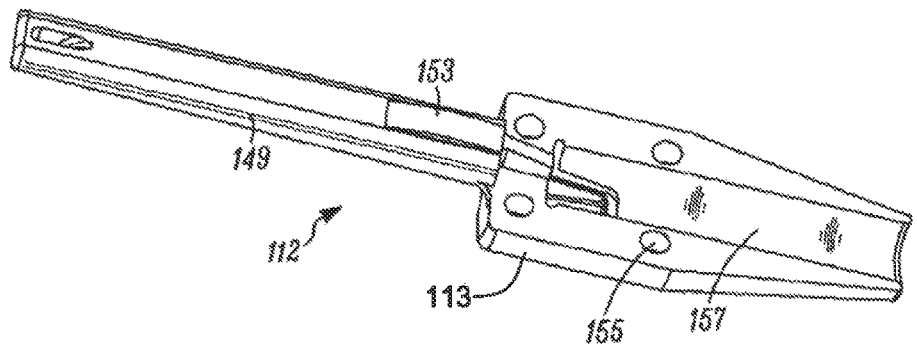
FIGS. 5A-D are perspective views of an implant device and associated components, according to an example of the present disclosure.
Figure 5B:
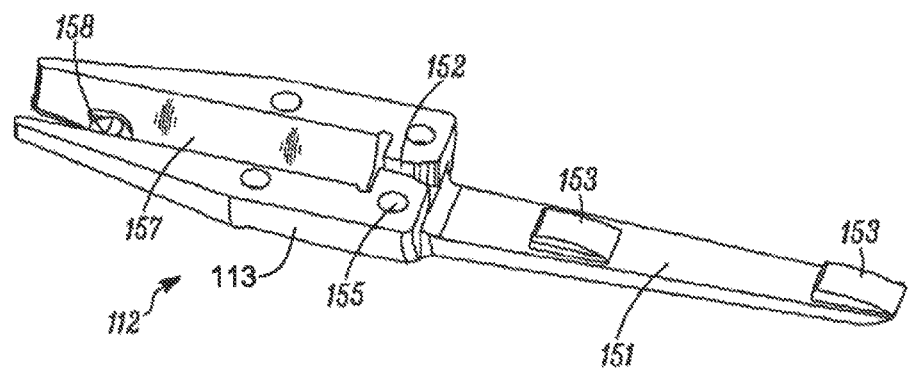
Figure 5C:
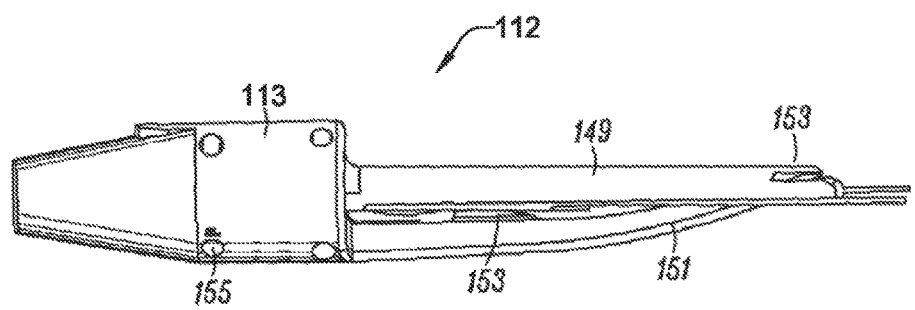

FIGS. 5A-5D provide perspective views of implant device 112. Implant device 112 can be of one-piece construction or multi-component construction. For example, implant device 112 is shown as including upper and lower components in FIGS. 5A-B. The upper component includes upper beam 149 (FIG. 5A) and the lower component includes lower beam 151 (FIG. 5B). FIG. 5C provides one perspective view of implant device 112 including aligned upper and lower components. In at least some examples, as described previously, implant 114 may be disposed between upper beam 149 and lower beam 151, and upper beam 149 and lower beam 151 may releasably retain implant 114. For instance, upper beam 149 and lower beam 151 may passively retain implant 114 when implant 114 is positioned between upper beam 149 and lower beam 151, such as by contact forces between upper beam 149 and implant 114 and lower beam 151 and implant 114. In other examples, implant device 112 may include an activate retention mechanism to retain implant 114. The active retention mechanism may require manipulation by a user to retain and/or release implant 114. Additionally, in at least some examples, implant positioning component 115 is connected to upper beam 151. When implant 114 is disposed between upper beam 149 and lower beam 151, implant 114 may be positioned such that implant positioning component 115 engages the first face of implant 114 along with upper beam 149. In some examples, securing mechanism 152 holds the implant positioning component 115 to the head 113. For instance, securing mechanism 152 may be a slot that holds a T-shaped protrusion on a proximal portion of the implant positioning component 115. However, in other examples, implant positioning component 115 may be connected to head 113 in a different manner or even to lower beam 151, if desired.

As described previously, implant device 112 may include a hollow portion which engages with inner tube 110. Accordingly, implant device 112 may include inner tube interface component 157 positioned at head 113. Inner tube 110 may slide into inner tube interface component 157 which may secure inner tube 110 to head 113. In the example of FIGS. 5A-5D, inner tube interface component 157 is a channel within head 113. When the channel receives inner tube 110, inner tube 110 may lock in place via an interference or friction fit or with locking mechanism 158. In some examples, locking mechanism may include a tab that interfaces with a slot or recess in inner tube 110. In examples where implant device 112 comprises two separate sections, the upper and lower components (as shown in FIGS. 5A and 5B) may be joined by fasteners and fastener holes 155. Fasteners and fastener holes 155 may comprise, for example, posts, protrusions, tabs or other securing mechanisms known to those skilled in the art which are capable of securing the two separate sections of implant device 112.

In some examples, implant device 112 may additionally include one or more gripping components 153. Gripping components 153 can be positioned on or integrated with one or more of upper beam 149 and lower beam 151. In the example of FIGS. 5A-5D, implant device 112 comprises one gripping component 153 on upper beam 149 and two gripping components 153 integrated on lower beam 151, but in other examples, the amount and location of gripping components 153 may vary. Gripping components 153 may assist in securing implant 114. For example, gripping components may have both curved and straight edges, thereby facilitating movement of implant 114 in a first direction, but resisting movement of implant 114 in other directions. In the example of FIGS. 5A-5D, gripping components 153 have first, curved edges which face in a distal direction relative to head 113. A sloping surface extends away from the first, curved edges toward head 113 and, along with the side and back surfaces of gripping components 153, produces angular edges on the sides and the back (near head 113) of gripping components 153. When loading implant 114 between upper beam 149 and lower beam 151, the first, curved edge and sloping surface of gripping components 153 may allow implant 114 to be slid between upper beam 149 and lower beam 151 toward head 113 with a relatively low amount of force. However, the angular edges of gripping components 153 may resist movement of implant 114 in a direction away from head 113 and laterally to head 113. For example, as described above, implant 114 may comprise a soft material, and the soft material may catch on the angular edges of gripping components 153. Accordingly, gripping components 153 may be configured to require relatively more force to move implant 114 away from head 113 or laterally to head 113, thereby helping to secure implant 114 once implant 114 has been positioned between upper beam 149 and lower beam 151.

In other examples, gripping components 153 can include a textured surface or rounded edges. In still other examples, one of or both of the upper beam 149 and lower beam 151 can comprise one or more ribs, protrusions, bumps, posts, tabs, etc. Accordingly, implant device 112 may include one or more of such features, all of which may help to secure implant 114 between upper beam 149 and lower beam 151, or adjust the relative levels of force required to position implant 114 between upper beam 149 and lower beam 151 or to move implant 114 away or laterally from head 113 once implant 114 is positioned between upper beam 149 and lower beam 151.

Figure 5D:
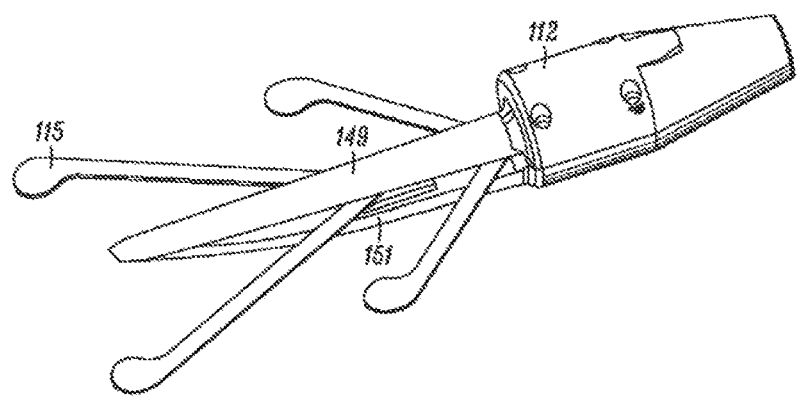

FIG. 5D shows implant device 112 fully assembled, including implant positioning component 115. In the example of FIG. 5D, implant positioning component 115 is shown in a deployed state and is depicted as four flat heads protruding on straight arms at an angle from upper beam 149 and lower beam 151. In the undeployed state, implant positioning component 115 may be configured to fit within sheath 103. Accordingly, in such an example, each arm of implant positioning component 115 may deform in a manner to allow insertion of implant device 112 into sheath 103. Accordingly, implant positioning component 115 may generally be flexible, and in the example of FIG. 5D, each arm of implant positioning component 115 may bend, twist, fold, wrap or otherwise deform in order for implant device 112 to fit within sheath 103.

In at least some examples, implant positioning component 115 is made of a material that may deform elastically into one or more shapes in order to fit within the confines of sheath 103. Some suitable example materials include metals and metal alloys including stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some examples, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some examples, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In other examples, implant positioning component 115 may be constructed of one or more of the above described materials configured as an inlay. For instance, implant positioning component 115 may comprise a metal structure encased in one or more other materials, such as a plastic or silicone material. The plastic or silicone material may be molded either completely or partly over the metal structure. Such hybrid-material structures may reduce the manufacturing cost of producing implant positioning component 115 or provide implant positioning component 115 with physical properties unable to be achieved by using only metal.

Figure 6:
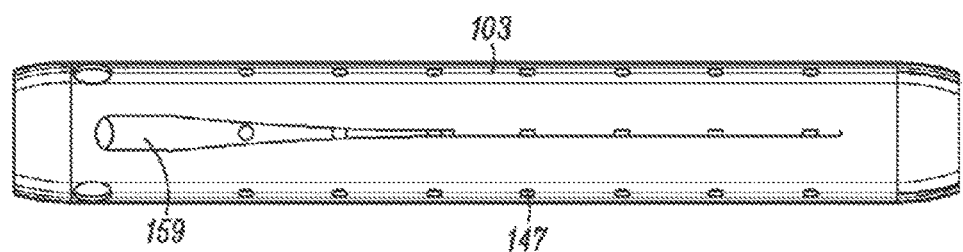
FIG. 6 is a perspective view of a sheath, according to an example of the present disclosure.

FIG. 6 is a perspective view of sheath 103. Sheath 103 may include sheath holes 147, which permit passage of liquids into the interior of sheath 103. For example, before a procedure, sheath 103, or implant device 112, and/or implant 114, may be in an unsterilized state. A user may place sheath 103, which is disposed around implant device 112 and implant 114 in a sterilization solution. Sheath holes 147 may permit the sterilization to permeate all portions of sheath 103, implant device 112, and implant 114. In other examples, implant 114 may be in a sterilized state, and sheath 103 may be placed in a hydrating or therapeutic solution. The hydrating or therapeutic solution may also permeate through sheath holes 147 and implant 114 may absorb the solution and hydrate and/or absorb the therapeutic solution which, when implanted, may operate in conjunction with implant 114 to heal an injury of a patient.

In some examples, sheath 103 may also include sheath slit 159. In some examples, sheath slit 159 may serve to allow a guidewire inserted into sheath 103 at a distal end relative to sheath slit 159 to pass out of sheath 103. For example, when sheath 103 is disposed around implant device 112, sheath slit 159 may align with lower beam 151 and, more specifically, groove 193 of lower beam 151. In such an example, when a guidewire is inserted into sheath 103, the guidewire may follow groove 193 of lower beam 151 and may continue out of sheath 103 through sheath slit 159. In some examples, after passing out through sheath slit 159, the guidewire may then enter into inner tube 110 where the guidewire may be advanced all the way to stopper 135. In additional examples, one or both ends of the sheath 103 can be tapered to fit to implant device 112 and/or engagement head 108 in order to provide less interference when cartridge 117 is inserted into the patient during a procedure. In still other examples, sheath 103 may be opaque, transparent or translucent. In at least some examples, at least a distal portion of sheath 103 is transparent or translucent so that implant 114 disposed within sheath 103 can be inspected to observe how implant 114 is disposed around implant device 112 within sheath 103. As described previously, sheath 103 may be slidable with respect to implant device 112 and implant 114 when such components are disposed within sheath 103.

Figure 7:
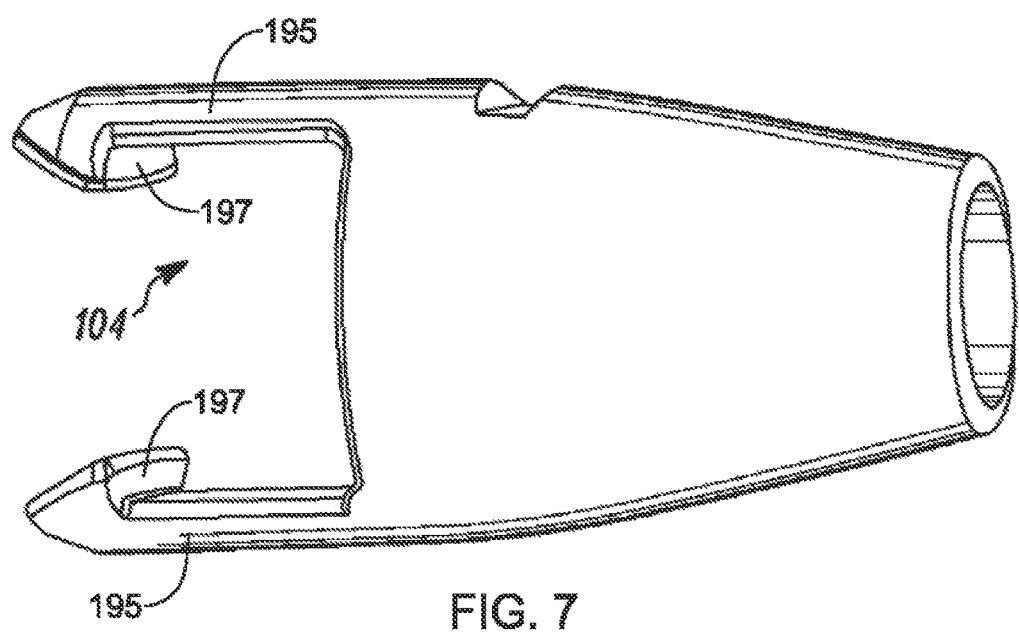
FIG. 7 is a perspective view of a connector, according to an example of the present disclosure.

FIG. 7 is a perspective view of a connector 104. Outer tube 102 may engage with a proximal end of connector 104, and engagement head 108 may engage with connector 104 at a distal end of connector 104. Connector 104 may comprise one or more engagement arms 195, and the one or more engagement arms may include engagement features, such as latches 197, in some instances. Each latch 197 may be configured to engage with a notch 199 or other engagement feature on engagement head 108 (shown in FIG. 11V). For example, each engagement arm 195 may extend axially along a length of connector 104. Each latch 197 may include a portion that extends generally perpendicular, or at a shallow angle relative to perpendicular, to the axis along which the engagement arms 195 extend. The one or more engagement arms 195 may form a cavity there between in which engagement head 108 may occupy when engaged with connector 104. The generally perpendicular portions of latches 197 may engagement with notches 199 to securely connect sheath 108 to outer tube 102. In some examples, engagement arms 195 may be flexible enough where, when engaged with engagement head 108, engagement arms 195 may be bent far enough away from engagement head 108 such that the generally perpendicular portions of latches 197 disengage from notches 199, thereby allowing sheath 108 to be disconnected from connector 104. In at least some examples, the generally perpendicular portions of latches 197 and notches 199 may be configured such that a force applied generally parallel to engagement arms 195 may cause engagement arms 195 to bend enough to disconnect connector 104 from sheath 103. In other instances, connector 104 may include other engagement features configured to mate with engagement features of engagement head 108.

Figure 8A:
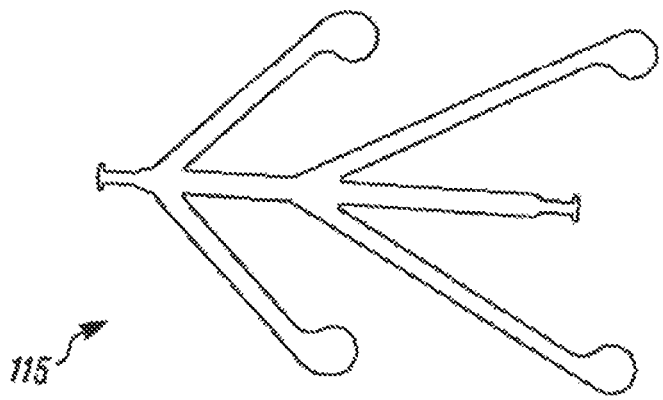
FIGS. 8A-I are top views of exemplary implant positioning components, according to examples of the present disclosure.

FIGS. 8A-8I all depict example configurations of implant positioning component 115. Although FIG. 8A depicts an example configuration consistent with the configurations depicted in FIG. 5D, implant positioning component 115 can be shaped in any number of different configurations. For instance, in some examples implant positioning component 115 may be shaped to maximize surface area contact with implant 114 while still retaining the size and shape to fold within the sheath 103 in the undeployed state. In other examples, implant positioning component 115 may be shaped to minimize trauma to implant 114 in the undeployed state and during deployment.

Figure 8B:
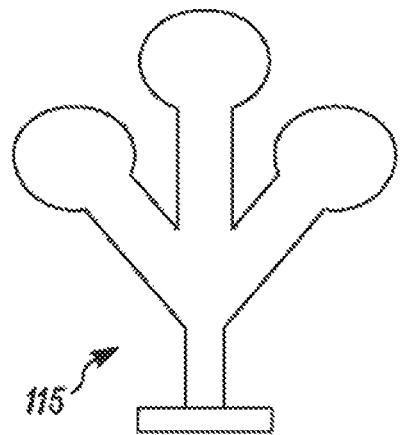
Figure 8C:
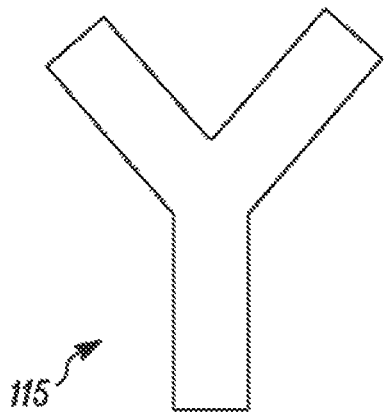
Figure 8D:
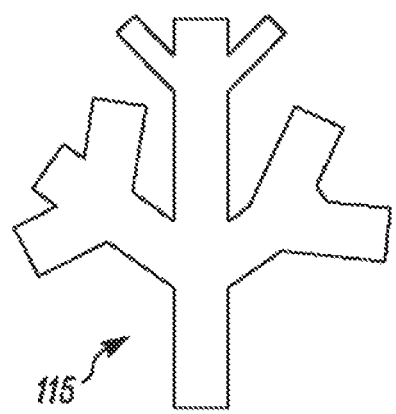
Figure 8E:
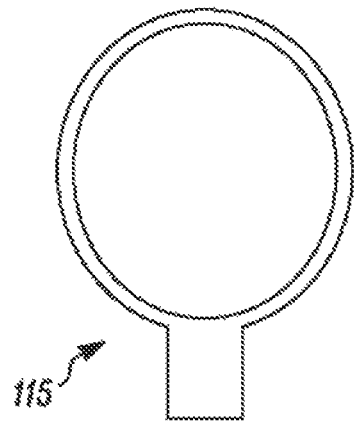
Figure 8F:
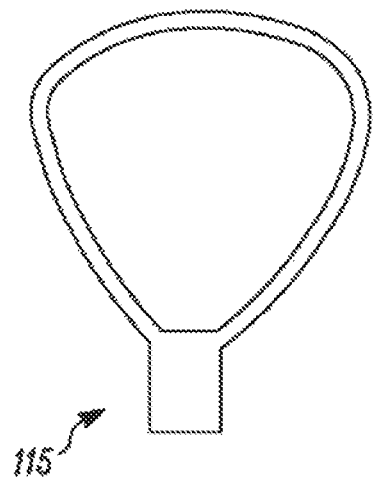
Figure 8G:
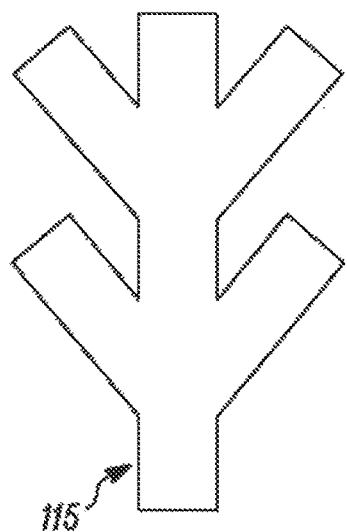
Figure 8H:
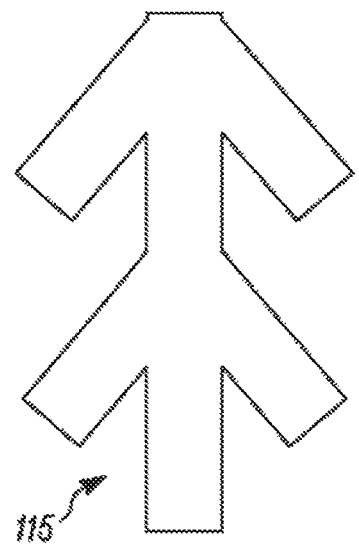
Figure 8I:
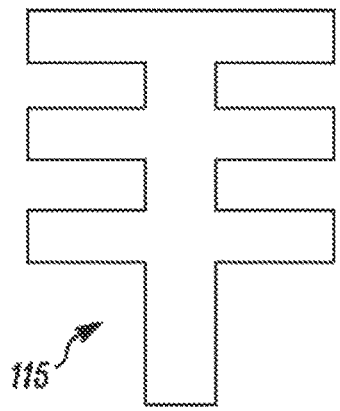

In some configurations, implant positioning component 115 may include a main trunk extending in a longitudinal direction and one or more appendages that extend away from the trunk at an angle, for example as shown in FIGS. 8B-8D and 8G-8I. FIG. 8B depicts implant positioning component 115 with a main trunk with a larger, round portion or head at a distal end. Two appendages extend away from the main trunk beginning at approximately half way between the distal end of the main trunk and the proximal end of the main trunk. The two appendages extend outward at an angle in a direction away from the proximal end of the main trunk and also terminate in larger, round heads. FIG. 8C also includes a main trunk, but instead of ending in a larger, round head, the main trunk splits into two appendages at the distal end of the main trunk. As with FIG. 8B, the two appendages extend away from the main trunk at an angle and away from the proximal end of the main trunk. FIG. 8D depicts a similar implant positioning component 115 to FIG. 8B, except instead of ending in larger, round heads, each of the main trunk and appendages split into additional appendages, which extend away at an angle from the trunk or appendage from which the additional appendages split. In FIG. 8G, implant positioning component 115 includes multiple sets of appendages which split from the main trunk. In FIG. 8H, implant positioning component 115 includes appendages that, instead of extending away from a proximal end of the main trunk, extend toward the proximal end of the main trunk. In FIG. 8I, implant positioning component 115 includes appendages that extend generally perpendicular to the main trunk.

Although the variations of the appendages and main trunk segments of FIGS. 8A-8D and 8G-8I were depicted with various features, such as being straight, ending in larger, flat heads, extending toward, away, or perpendicular to a proximal end of the main trunk, any of the examples could include any of such features. For example, in FIG. 8C, the appendages of implant positioning component 115 may include larger, round heads, if desired. In other examples, the appendages may extend toward the proximal end of the main trunk and include larger, round heads, if desired. Accordingly, the various features of each of FIGS. 8A-8D and 8G-8I may be combined without deviating from any disclosure of implant positioning component 115.

FIGS. 8E and 8F depict additional examples of implant positioning component 115. For instance, FIG. 8E depicts implant positioning component 115 including a main trunk that terminates at a distal end with an annular appendage including an opening. In FIG. 8F, implant positioning component 115 is depicted in similar manner to implant positioning component 115 in FIG. 8E, except that the main trunk ends in a rounded triangle shape appendage with an opening in the middle rather than a circle. In still other examples, implant positioning component 115 may include appendages with openings which create other shapes at an end of the main trunk.

Figure 9A:
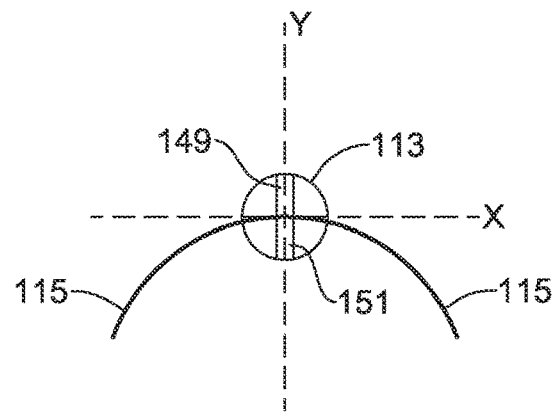
FIGS. 9A-C are perspective views on an axis showing an implant device component geometry, according to an example of the present disclosure.
Figure 9B:
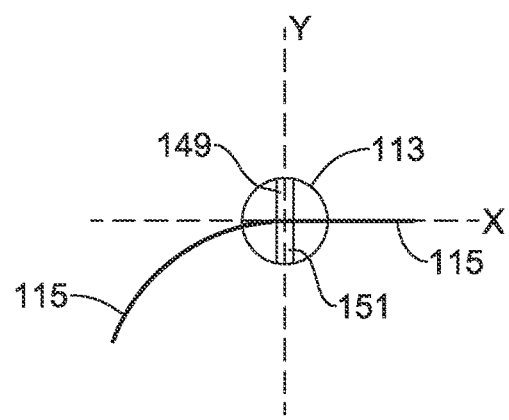
Figure 9C:
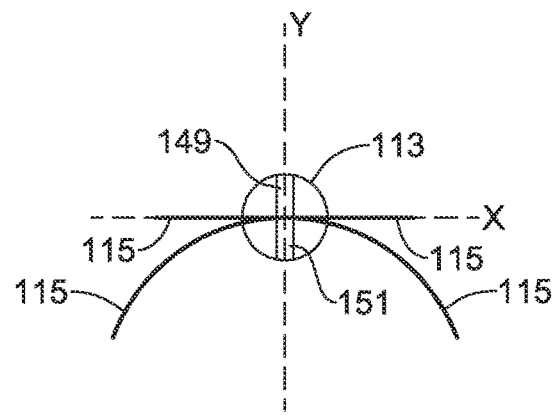

FIGS. 9A-C depict other features of at least some example implant positioning component 115. FIGS. 9A-C depict a perspective view looking down implant device 112 from the ends of upper beam 149 and lower beam 151 toward head 113. FIG. 9A depicts implant positioning component 115 bending out of a plane, or a parallel plane, that runs laterally through implant device 112. In examples where implant positioning component 115 has such a configuration in a resting state as in FIG. 9A, when elastically deformed in the undeployed state, implant positioning component 115 may impart force on implant 114 when implant 114 is disposed around upper beam 149 and implant positioning component 115. For instance, as described previously, in the undeployed state, implant device 112, including implant positioning component 115, may be positioned within sheath 103, and implant 114 may be disposed at least partially around implant device 112, including implant positioning component 115. Additionally, in order for implant positioning component 115 to fit within sheath 103, implant positioning component 115 may need to be elastically deformed away from a resting state. Accordingly, when sheath 103 is retracted, implant positioning component 115 may bend, twist, unfold, unwrap or otherwise attempt to un-deform or revert back to a resting state. This may impart a force on implant 114, which is at least partially disposed around implant positioning component 115. This force may cause implant 114 to unfold or unfurl into a generally flat shape, according to the interaction between the one or more components of implant positioning component 115 and implant 114.

Of course, in other examples, implant positioning component 115 may take other shapes with different resting states. For example, FIG. 9B depicts an exemplary portion, for example one side, of implant positioning component 115 may have a resting state that is out of a plane that runs laterally through implant device 112, or a parallel plane, while the other portion, or other side, of implant positioning component 115 has a resting state that is in the plane or in a parallel plane. In still other examples, such as depicted in FIG. 9C, implant positioning component 115 may include a distal (or proximal) portion that has a resting state out of plane with a plane that run laterally through implant device 112, or a parallel plane, while a proximal portion (or distal portion) of implant positioning component 115 has a resting state in the plane that runs laterally through implant device 112, or a parallel plane. For instance, in various examples only the distal portion of implant positioning component 115 that has a resting state out of plane or that runs laterally through implant device 112, or a parallel plane, may comprise the distal 50%, distal 25% or distal 10% of implant positioning component 115. Additionally, although example implant positioning component 115 were shown as curving out of a plane, in other examples implant positioning component 115 may angle away from a plane or otherwise deviate from the plane. In some examples, implant positioning component 115 may have one bend, curve, or angle at a proximal portion and a differing bend, curve, or angle at a distal portion.

Figure 10A:
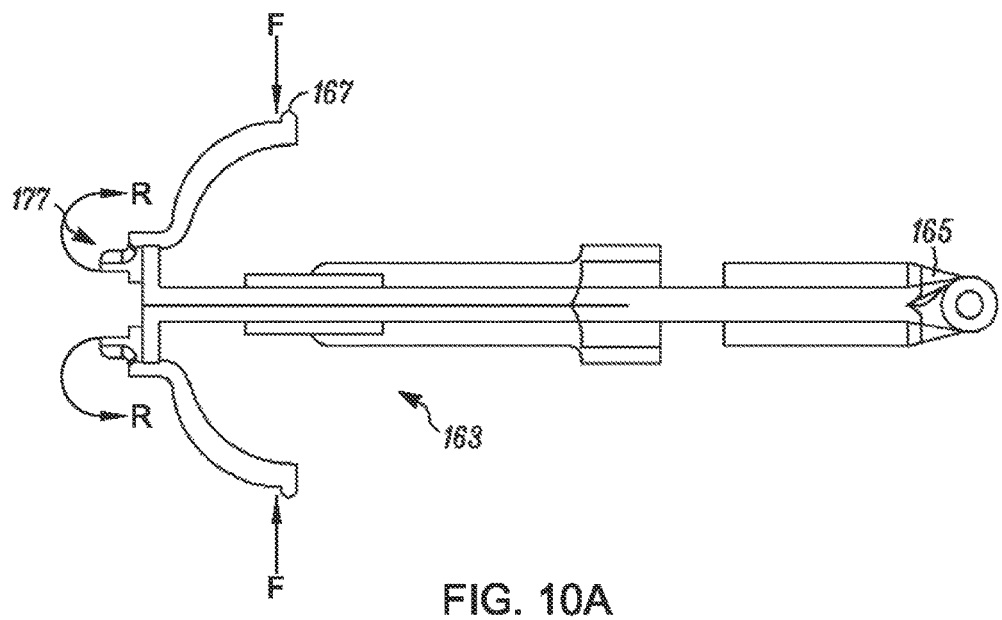
FIGS. 10A-D are perspective views of an implant cartridge loading vessel and associated components, according to an example of the present disclosure.
Figure 10B:
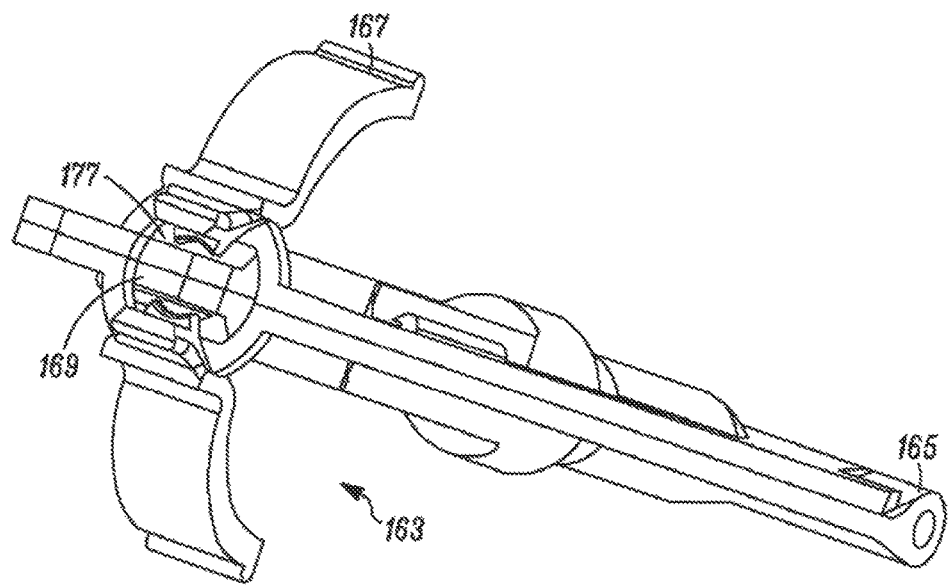
Figure 10C:
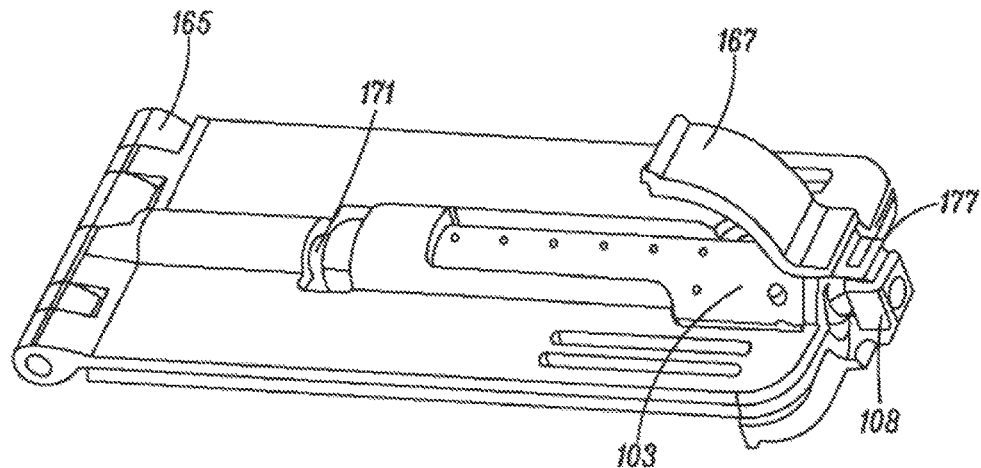
Figure 10D:
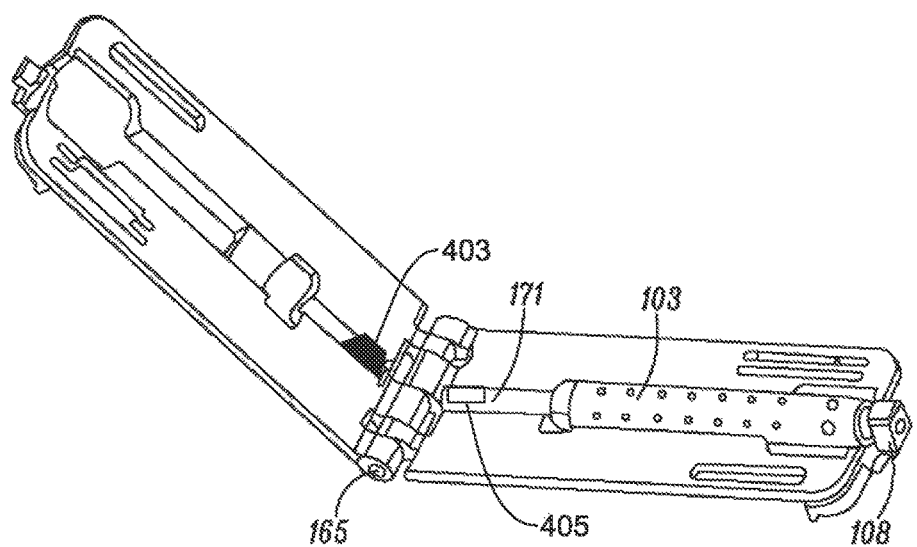

FIGS. 10A-10D depict views of implant cartridge loading vessel 163. FIG. 10A illustrates a side view of an empty, closed implant cartridge loading vessel 163. Implant cartridge loading vessel 163 includes hinge 165, release mechanisms 167, and sheath head engagement portions 177. Hinge 165 allows for movement of a first half of implant cartridge loading vessel 163 away from a second half of implant cartridge loading vessel 163, as seen in FIG. 8D. In some examples, sheath head engagement portions 177 include curved portions which create a curved opening (see FIG. 10B). In such examples, sheath head engagement portions 177 may engage with a cylindrical neck portion (see FIG. 12Q) of sheath 103 between sheath 103 and engagement head 108 of sheath 103. The cylindrical neck portion may have a diameter smaller than a diameter of engagement head 108 and sheath 103. Accordingly, when sheath 103 is loaded into implant cartridge loading vessel 163, implant cartridge loading vessel 163, when closed, may prevent removal of sheath 103 from implant cartridge loading vessel 163 due to sheath head engagement portions 177 engaging with the cylindrical neck portion of sheath 103. FIG. 10C depicts sheath 103 engaged with implant cartridge loading vessel 163. Implant cartridge loading vessel 163 may include one or more channels sized appropriately for sheath 103 and loading tube 171 (described below), as seen in FIGS. 10C and 10D.

In order to release sheath 103 from implant cartridge loading vessel 163, a force may be applied to release mechanisms 167 in the direction of force arrows F in FIG. 10A. Release mechanisms 167 may be made of a flexible material such that when a force is applied in the direction of force arrows F, release mechanisms 167 may cause connected sheath head engagement portions 177 to move or pivot generally in the directions of reaction arrows R. Moving or pivoting sheath head engagement portions 177 generally in the directions of reaction arrows R causes the opening formed by sheath head engagement portions 177 to widen. This widening action may spread the diameter of the opening formed by sheath head engagement portions 177 to become greater than the diameter of sheath 103, thereby allowing sheath 103 to be pulled out of implant cartridge loading vessel 163.

In some examples, implant cartridge loading vessel 163 may comprise a material that does not change in the presence of conventional sterilization solutions. Accordingly, a user may soak implant cartridge loading vessel 163 containing sheath 103, implant device 112, and implant 114 in a sterilizing and/or hydrating solution before using implant cartridge loading vessel 163 to load cartridge 117 onto device 101, for example by connecting engagement head 108 to connector 103. As seen in FIGS. 10C and 10D, implant cartridge loading vessel 163 includes openings which would allow a sterilizing and/or hydrating solution, or any other fluid, to reach sheath 103, and thereby permeate through sheath holes 147 and reach implant device 112 and implant 114. Additionally, in some examples, the assembly of sheath 103, implant device 112, implant 114, loading tube and implant cartridge loading vessel 163 may be stored, packaged, shipped, etc. until ready to for sterilization and/or hydration of implant 114, or attachment to the delivery device 101 at the time of a procedure. Accordingly, attachment of cartridge 117 to device 101 may occur just before implanting implant 114 within a patient, such as intraoperative during the implant procedure. However, in other examples, cartridge 117 may be attached to device 101 before delivery to a user. In such examples, a user may merely need to dip the end of device 101, e.g. cartridge 117, in a sterilizing and/or hydrating solution just prior to implanting implant 101 within a patient.

Figure 11A:
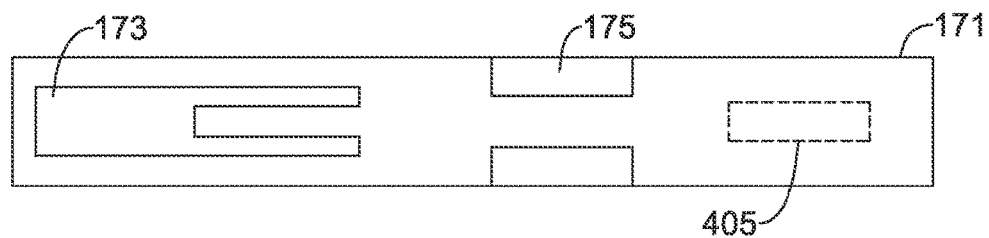
FIGS. 11A-C are perspective views of loading tubes, according to examples of the present disclosure.
Figure 11B:
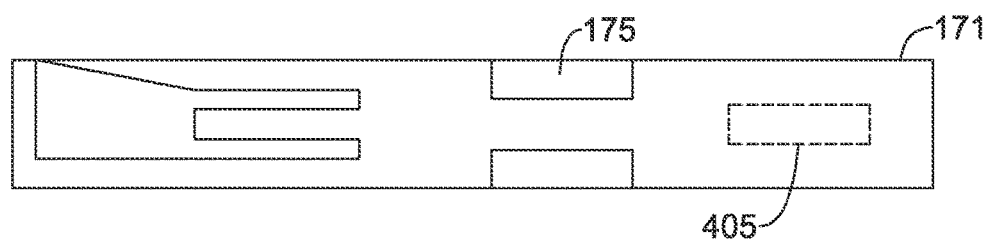
Figure 11C:
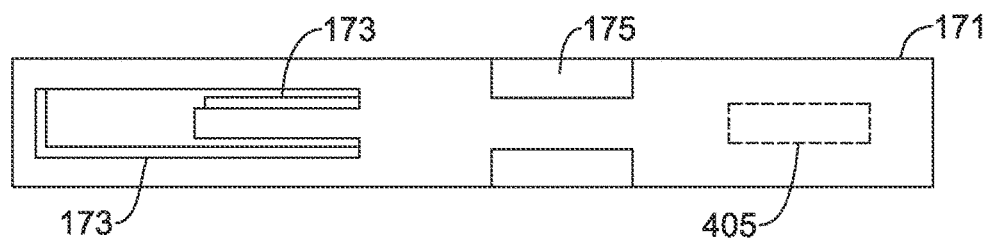

In some examples, loading tube 171 (examples of loading tube 171 are shown in FIGS. 11A-11C) may also be held by implant cartridge loading vessel 163. For example, as explained with respect to FIGS. 11A-C and 12A-12V, loading tube 171 may be used to configure sheath 103, implant device 112, and implant 114 into the undeployed state. Accordingly, after using loading tube 171 to configure sheath 103, implant device 112, and implant 114 into the undeployed state, the entire assembly, including loading tube 171, may be loaded into implant cartridge loading vessel 163. Once loaded, implant cartridge loading vessel 163 and the loaded components may be positioned so engagement head 108 engages with engagement arms 189 of connector 104 of device 101. Once engagement head 108 is engaged with engagement arms 189 on device 101, a user may apply force to release mechanisms 167 and pull implant cartridge loading vessel 163, thereby removing implant cartridge loading vessel 163 from sheath 103 and device 101. In some examples, such as the example depicted in FIG. 10D, implant cartridge loading vessel 163 may additionally include raised tab 403. Raised tab 403 may securely engage with loading tube slot 405 when the two halves of implant cartridge loading vessel 163 are closed. Accordingly, after attaching engagement head 108 to engagement arms 189 and removing implant cartridge loading vessel 163, loading tube 171 may additionally be removed by remaining in implant cartridge loading vessel 163 and secured by raised tab 403 engaged with loading tube slot 405. In such examples, removing implant cartridge loading vessel 163 removes all components from device 101 not intended to be inserted into the patient during placement of implant device 112 and implant 114. Additionally in such examples, with loading tube 171 removed from engagement with implant positioning component 115, sheath 103 may then hold implant positioning component 115 in the undeployed position until a force causes sheath 103 to retract away from implant device 112 and implant 114.

As mentioned above, FIGS. 11A-11C illustrate examples of loading tube 171. The perspective of FIGS. 11A and 11B is a perspective opposite that of where loading tube slot 405 is positioned on loading tube 171. As depicted in FIG. 11A, loading tube 171 may additionally include first implant positioning component slot 173 and second implant positioning component slots 175. As will be described below with respect to FIGS. 12A-12V, one or more appendages or other features of implant positioning component 115 may engage with first implant positioning component slot 173 and second implant positioning component slots 175 in order to position and retain implant positioning component 115 in an undeployed state.

FIG. 11B depicts example loading tube 171 with first implant positioning component slot 173 shaped differently from first implant positioning component slot 173 of example loading tube 171 depicted in FIG. 11A. In FIG. 11A, first implant positioning component slot 173 comprises a cut-out portion of a wall of loading tube 171 including three portions which connect at substantially right angles. The three portions create a tab in the middle of the cut-out portion of the wall of loading tube 171. FIG. 11B depicts a similar cut out portion of the wall of loading tube 171, except that one edge of the cut-out portion includes an angled portion. Such an angled portion may provide a greater opening for engaging implant positioning component 115. FIG. 11C depicts yet another example loading tube 171. In FIG. 11C, first implant positioning component slot 173 may be positioned on the same side of loading tube 171. Additionally, loading tube 171 may have another first implant positioning component slot 173 (shown in dashed lines) opposite the depicted first implant positioning component slot 173. Of course, other example loading tubes may be similar to loading tube 171 in FIG. 11C but have first implant positioning component slot 173 shaped similar to first implant positioning component slot 173 depicted in FIG. 11B. In still other examples, loading tube 171 may have differently shaped slots.

Figure 12A:
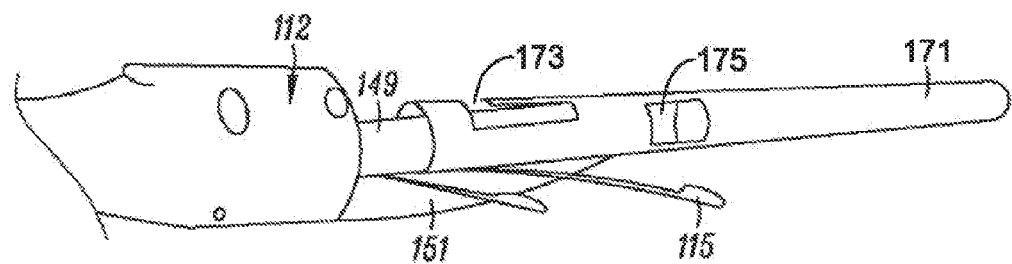
FIGS. 12A-V are perspective views of an implant positioning component and a loading tube, according to an example of the present disclosure.
Figure 12B:
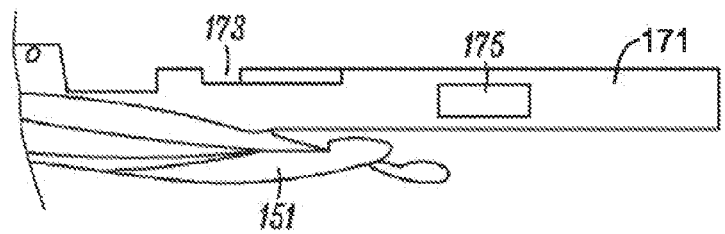
Figure 12C:
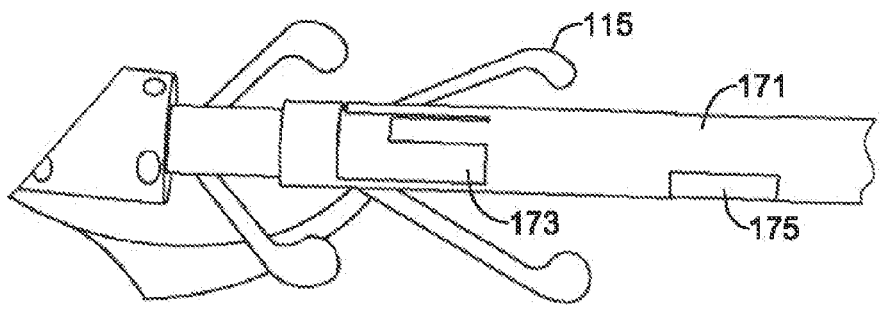
Figure 12D:
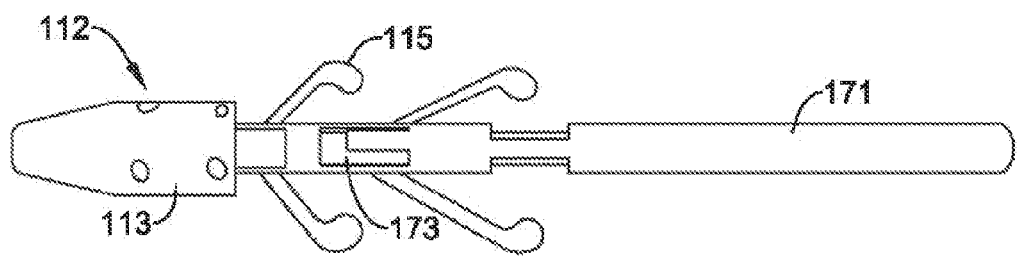
Figure 12E:
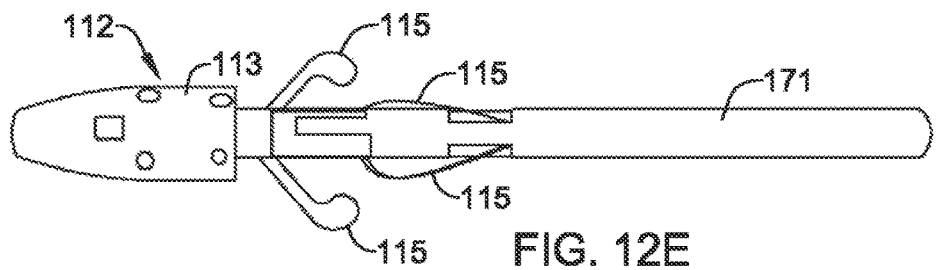
Figure 12F:
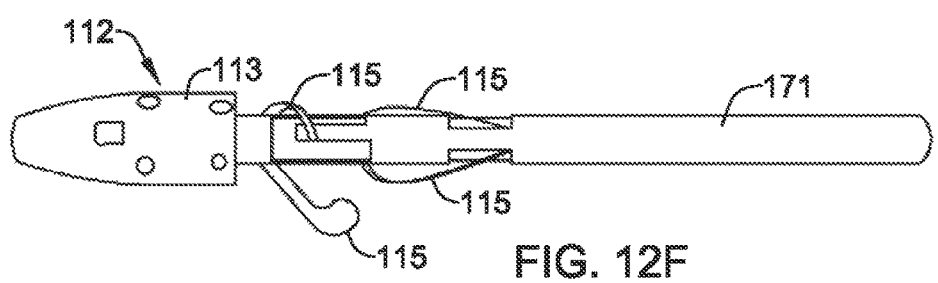
Figure 12G:
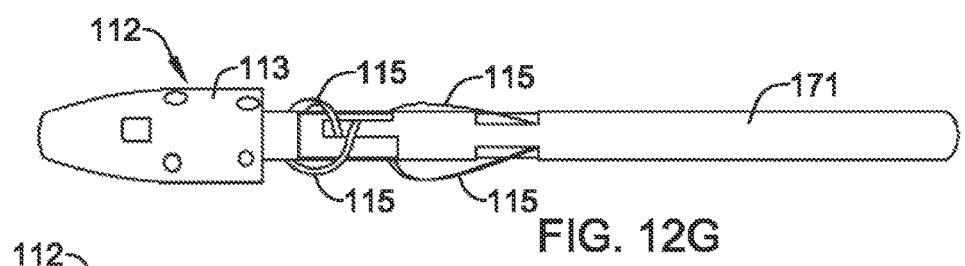
Figure 12H:
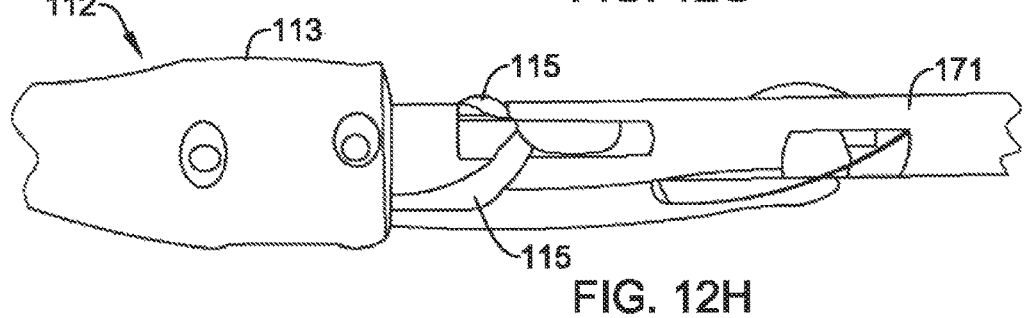
Figure 12I:
Figure 12N:
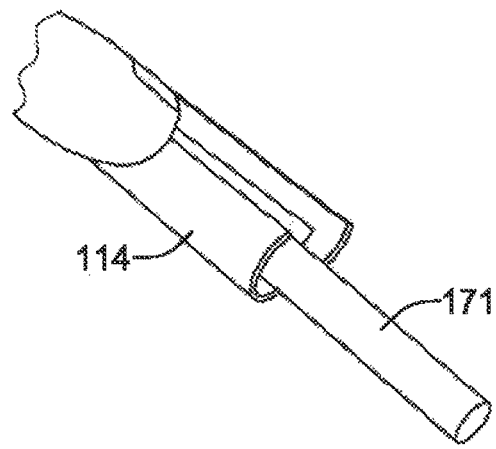
Figure 12O:
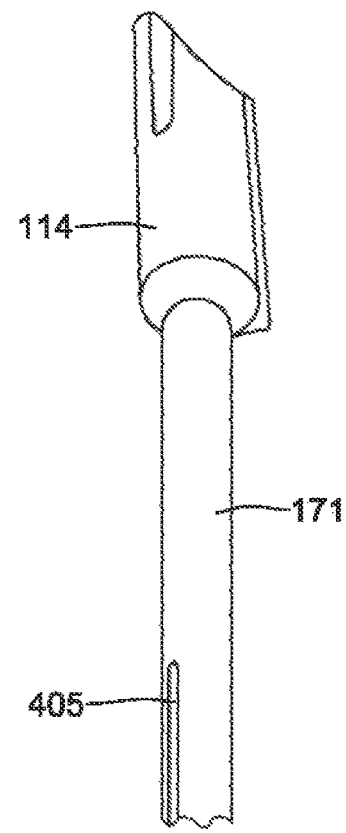
Figure 12P:
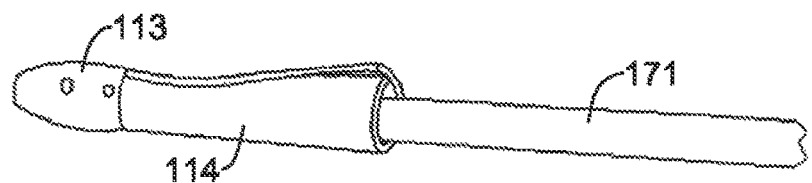
Figure 12Q:
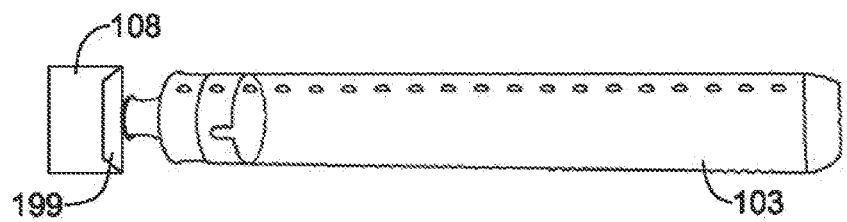
Figure 12R:
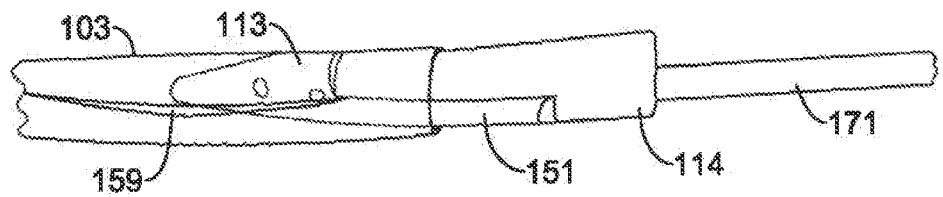
Figure 12S:
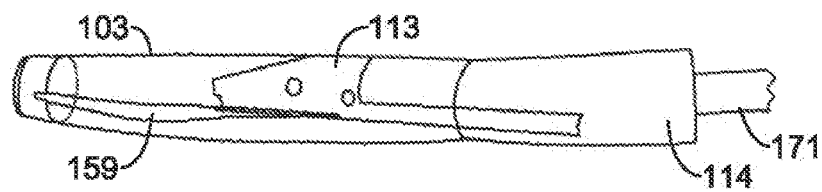
Figure 12T:
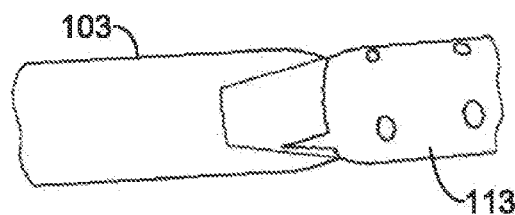
Figure 12U:
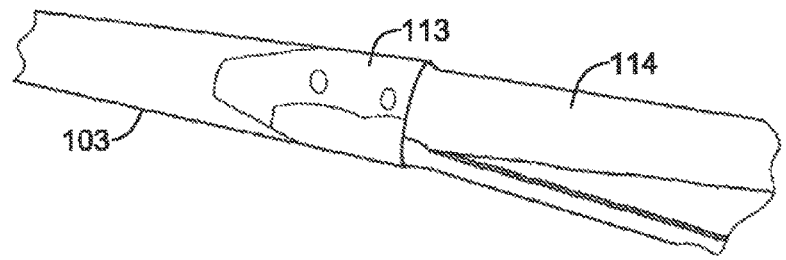
Figure 12V:
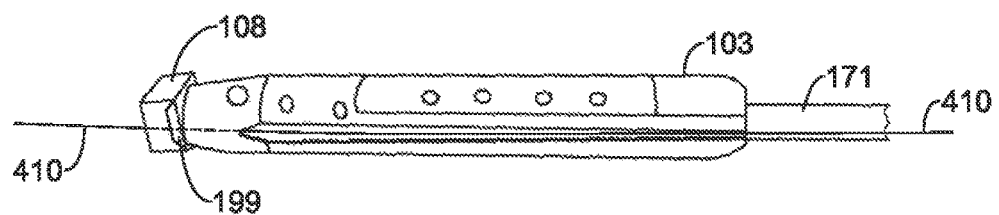

FIGS. 12A-12V depict various stages of loading implant device 112, implant 114, and loading tube 171 into sheath 103. For example, FIGS. 12A-12D depict various perspective views of loading tube 171 disposed on implant device 112. FIGS. 12A-12D depict loading tube 171 disposed at least partially over upper beam 149 such that second implant positioning component slots 175 are disposed outward laterally from implant device 112 and first implant positioning component slot 173 is disposed above upper beam 149. However, in other examples where loading tube 171 has differently placed or shaped first implant positioning component slots 173, the placement and/or shape of first implant positioning component slots 173 relative to implant device 112 may be different. For instance, in some examples, loading tube 171 may additionally include another first implant positioning component slot 173 disposed beneath upper beam 149. In other examples, first implant positioning component slots 173 may also be positioned on loading tube 171 such that first implant positioning components slots 173 are also disposed outward laterally from implant device 112.

FIGS. 12E-12I depict how implant positioning component 115 may be configured to engage with loading tube 171 such that implant positioning component 115 may be positioned into the undeployed state and retained in the undeployed state by loading tube 171. FIG. 12E illustrates how a portion of implant positioning component 115 may elastically deform in order to traverse second implant positioning component slots 175 into loading tube 171. Second implant positioning component slots 175 may be sized appropriately so that when a portion of implant positioning component 115 traverses second implant positioning component slots 175, second implant positioning component slots 175 may engage the portion of implant positioning component 115 residing within loading tube 171 to prevent the portion of implant positioning component 115 from retracting out of second implant positioning component slots 175 and returning to a resting state. In some examples, loading tube 171 may be positioned at a first location relative to head 113, and implant positioning component 115 may be deformed to engage with first implant positioning component slot 173 and second implant positioning component slots 175 when loading tube 171 is positioned at the first location, for example as in FIGS. 12E-12G. In such examples, after implant positioning component 115 has engaged with first implant positioning component slot 173 and second implant positioning component slots 175, loading tube 171 may be moved to a second position, such as contacting head 113, as depicted in FIG. 12H. Such movement of loading tube 171 may force the portions of implant positioning component 115 engaged with loading tube 171 further into loading tube 171, thereby creating a firmer engagement between implant positioning component 115 and loading tube 171. FIGS. 12H and 12I illustrate other perspective views of loading tube 171 engaged with implant positioning component 115 in the undeployed state.

FIGS. 12J-12M depict an example of how implant 114 may be disposed around implant device 112. FIGS. 12J and 12K depict implant 114 being positioned with respect to implant device 112. In at least some examples, implant 114 may be positioned such that an edge of implant 114 contacts head 113 of implant device 112. In other examples, implant 114 may be positioned away from head 113. In one example, as described previously, implant 114 is inserted between upper beam 149 and lower beam 151. In examples where one face of implant 114 is conditioned to be placed in contact with an area of the patient to be treated, implant 114 may be positioned so that such a face is in contact with lower beam 151. After positioning implant 114 appropriately with respect to implant device 112, implant 114 may be rolled, folded, wrapped, curled, or otherwise deformed at least partially around implant device 112, including upper beam 149 and implant positioning component 115, as depicted in FIGS. 12L and 12M.

FIGS. 12N-12P illustrate additional stages of disposing implant 114 at least partially around implant device 112. FIG. 12N illustrates that, in some examples, external input, such as through human force, may be necessary to roll, fold, wrap, curl, or otherwise deform implant 114 at least partially around implant device 112. In some examples, implant 114 may be large enough where on edge of implant 114 may overlap a second edge of implant 114 when implant is fully in position, as seen in FIGS. 12O and 12P.

FIGS. 12Q-12V illustrate implant device 112, implant 114, and loading tube 171 at various stages of loading into sheath 113. For example, FIG. 12Q depicts sheath 103 alone. FIGS. 12R-12U depict various perspectives of implant device 112, implant 114, and loading tube 171 loaded partially into sheath 103. FIG. 12R gives a perspective showing how lower beam 151 and sheath slit 159 may align during loading. FIG. 12T depicts sheath 103 with a tapered portion at the distal end of sheath 103, where the tapered portion has a notch cut-out to allow for expansion of the tapered portion during loading of implant device 112, implant 114, and loading tube 171. FIG. 12V depicts implant device 112, implant 114, and loading tube 171 loaded into sheath 103, creating implant cartridge 117. FIG. 12V additionally illustrates guidewire 410 and how guidewire 410 may traverse through implant cartridge 117 and more specifically through sheath 103 when loaded with implant device 112 and implant 114.

Figure 13:
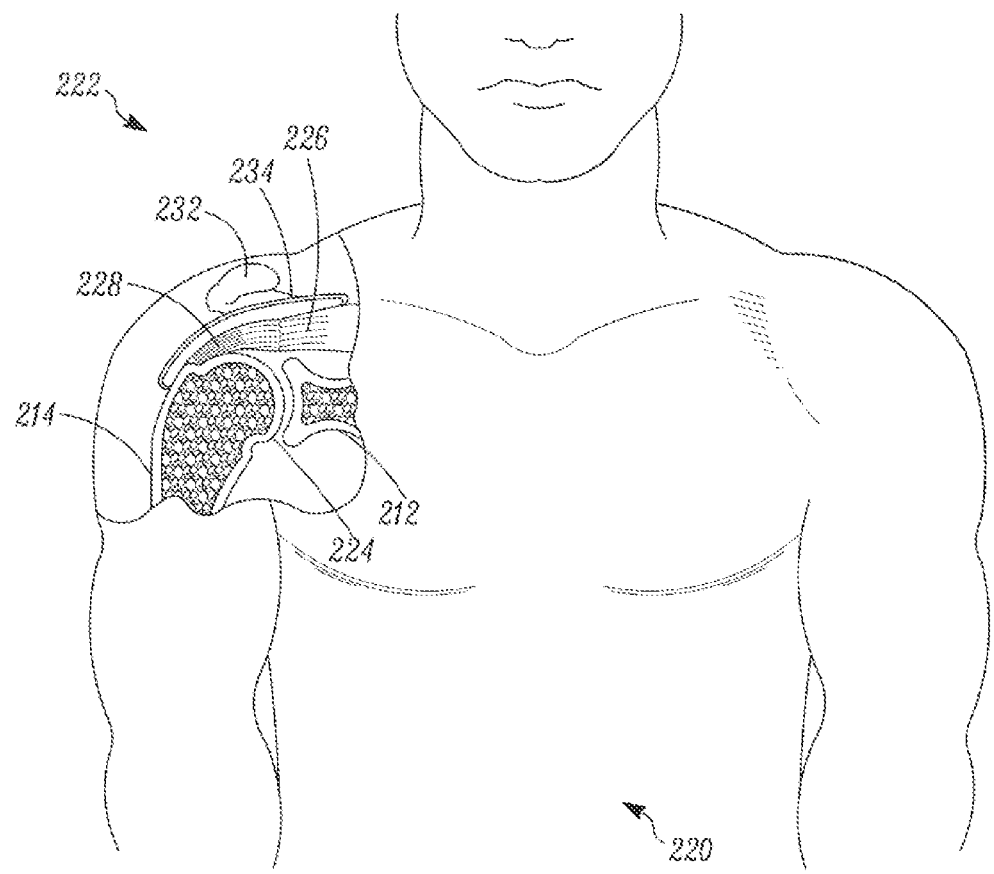
FIG. 13 is a stylized anterior view of a patient with a shoulder being shown in cross-section, according to an example of the present disclosure.

FIGS. 13-16M illustrate an exemplary use or application of implant delivery system 100. FIG. 13 is a stylized anterior view of patient 220. For purposes of illustration, shoulder 222 of patient 220 is shown in cross-section in FIG. 13. Shoulder 222 includes humerus 214 and scapula 212. In FIG. 13, head 224 of humerus 214 can be seen mating with a glenoid fossa of scapula 212 at a glenohumeral joint. The glenoid fossa comprises a shallow depression in scapula 212. The movement of humerus 214 relative to scapula 212 is controlled by a number of muscles including: the deltoid, the supraspinatus, the infraspinatus, the subscapularis, and the teres minor. For purposes of illustration, only supraspinatus 226 is shown in FIG. 13.

With reference to FIG. 13, distal tendon 228 of supraspinatus 226 meets humerus 214 at an insertion point. Scapula 212 of shoulder 222 includes acromion 232. Subacromial bursa 234 is shown extending between acromion 232 of scapula 212 and head 224 of humerus 214. Subacromial bursa 234 is shown overlaying supraspinatus 226 as well as supraspinatus tendon 228 and a portion of humerus 214. Subacromial bursa 234 is one of the hundreds of bursae found the human body. Each bursa comprises a fluid filled sac. The presence of these bursae in the body reduces friction between bodily tissues.

Exemplary implant delivery system 100 described herein may be used to position and deploy implant 114 to various target tissues throughout the body. The shoulder depicted in FIG. 13 is one example where implant 114 may be affixed to one or more bones associated with an articulating joint, such as the glenohumeral joint. Additionally, implant 114 may be affixed to one or more tendons to be treated. The tendons to be treated may be torn, partially torn, have internal microtears, be untorn, and/or be thinned due to age, injury or overuse. Implantation of implant 114 at such locations may provide beneficial therapeutic effect on a patient experiencing joint pain believed to be caused by partial thickness tears and/or internal microtears. In some cases, applying implant 114 early before a full tear or other injury develops may cause the tendon to thicken and/or at least partially repair itself, thereby avoiding more extensive joint damage, pain, and the need for more extensive joint repair surgery.

Figure 14:
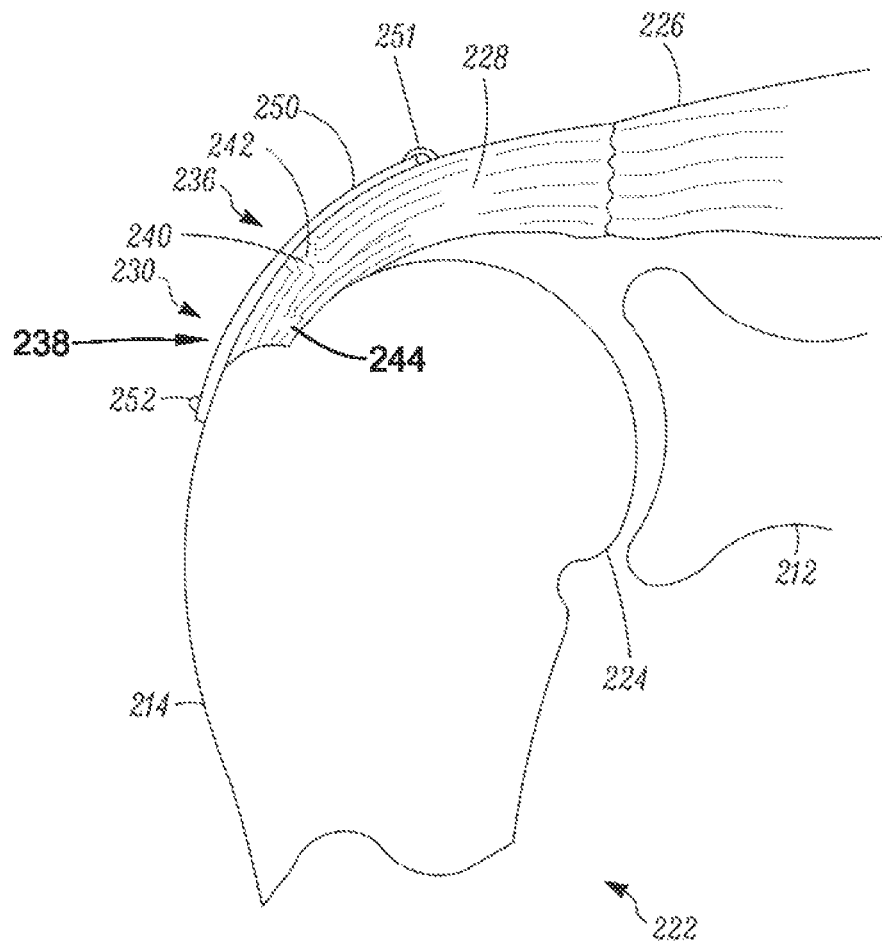
FIG. 14 is a stylized view of a shoulder depicting a head of the humerus shown mating with the glenoid fossa of the scapula at a glenohumeral joint and an implant affixed to a tendon, according to an according to an example of the present disclosure.

FIG. 14 is a stylized anterior view of shoulder 222 including humerus 214 and scapula 212. In FIG. 14, head 224 of humerus 214 is shown mating with a glenoid fossa of scapula 212 at a glenohumeral joint. Supraspinatus 226 is also shown in FIG. 14. This muscle, along with others, controls the movement of humerus 214 relative to scapula 212. Distal tendon 228 of supraspinatus 226 meets humerus 214 at insertion point 230.

As depicted in FIG. 14, distal tendon 228 includes first damaged portion 236. A number of loose tendon fibers 240 in first damaged portion 236 are visible in FIG. 14. First damaged portion 236 includes first tear 242 extending partially through distal tendon 228. First tear 242 may therefore be referred to as a partial thickness tear. With reference to FIG. 14, first tear 242 begins on the side of distal tendon 228 facing the subacromial bursa (shown FIG. 13) and ends midway through distal tendon 228. Accordingly, first tear 242 may be referred to as a bursal side tear.

With reference to FIG. 14, distal tendon 228 includes second damaged portion 238 located near insertion point 230. As illustrated, second damaged portion 238 of distal tendon 228 has become frayed and a number of loose tendon fibers 240 are visible. Second damaged portion 238 of distal tendon 228 includes second tear 244. Second tear 244 begins on the side of distal tendon 228 facing the center of the humeral head 224. Accordingly, second damaged portion 238 may be referred to as an articular side tear.

FIG. 14 illustrates sheet-like implant 250, which may be similar to implant 114 described above, which has been placed over the bursal side of distal tendon 228. Sheet-like implant 250 is affixed to distal tendon 228 by a plurality of tendon staples 251. Sheet-like implant 250 is affixed to humerus 214 by a plurality of bone staples 252. Sheet-like implant 250 extends over insertion point 230, first tear 242 and second tear 244. In other cases, sheet-like implant 250 may be placed on the bursal side of a tendon regardless of whether the tears being treated are on the bursal side, articular side or within the tendon. In some cases the exact location and nature of the tears being treated may be unknown. Sheet-like implant 250 may be applied to the bursal side of a tendon to treat shoulder pain that is most likely caused by one or more partial thickness tears in the tendon.

Figure 15A:
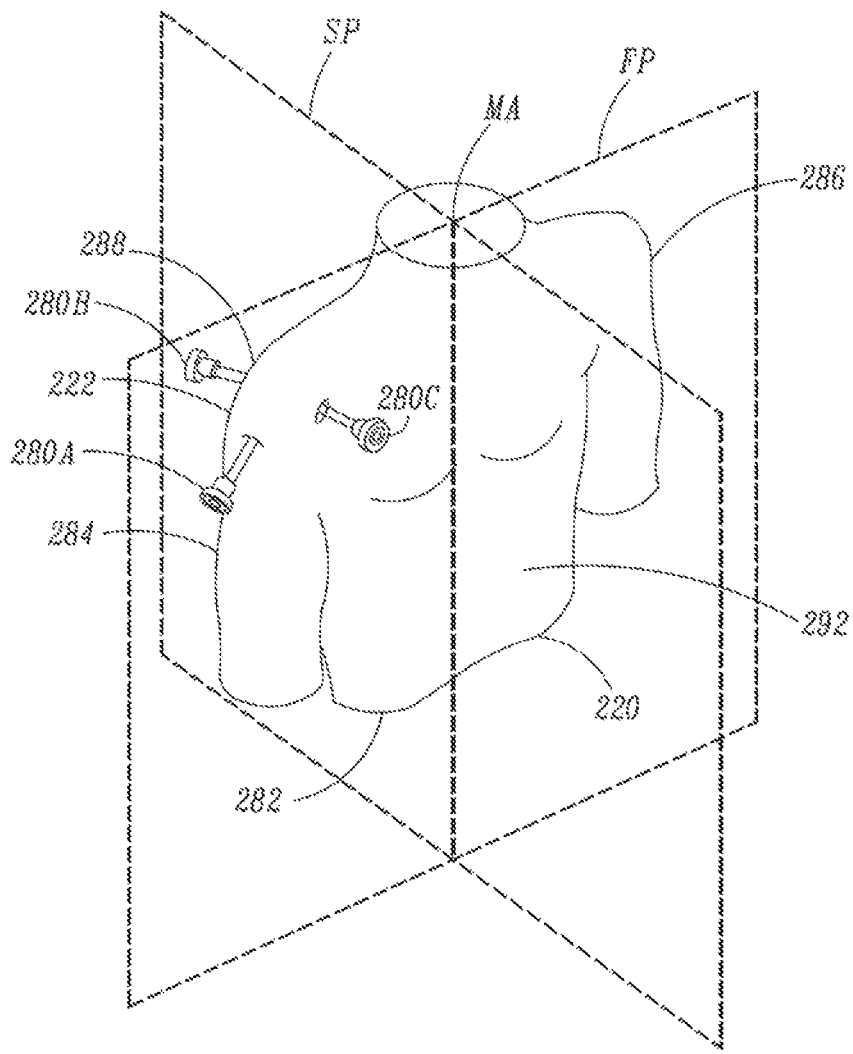
FIG. 15A is a stylized perspective view showing a portion of the body of a human patient divided into quadrants by planes, according to an example of the present disclosure.

FIG. 15A is a stylized perspective view showing a portion of body 282 of human patient 220. Body 282 includes shoulder 222. In the exemplary embodiment of FIG. 15A, a plurality of cannulas are positioned to access a treatment site within shoulder 222. In some cases, shoulder 222 may be inflated by pumping a continuous flow of saline through shoulder 222 to create a cavity proximate the treatment site. The cannulas shown in FIG. 15A include first cannula 280A, second cannula 280B and third cannula 280C.

In FIG. 15A, a sagital plane SP and a frontal plane FP are shown intersecting body 282. Sagital plane SP and frontal plane FP intersect one another at a medial axis MA of body 282. With reference to FIG. 15A, sagital plane SP bisects body 282 into a right side 284 and a left side 286. Also with reference to FIG. 15A, frontal plane FP divides body 282 into an anterior portion 292 and a posterior portion 288. Sagital plane SP and a frontal plane FP are generally perpendicular to one another. These planes and portions are used to describe the procedures used in exemplary embodiments.

First cannula 280A is accessing a treatment site within shoulder 222 using a lateral approach in which first cannula 280A pierces the outer surface of right side 284 of body 282. The term lateral approach could also be used to describe situations in which an instrument pierces the outer surface of left side 286 of body 282. Second cannula 280B is accessing a treatment site within shoulder 222 using a posterior approach in which second cannula 280B pierces the outer surface of posterior portion 288 of body 282. Third cannula 280C is accessing a treatment site within shoulder 222 using an anterior approach in which third cannula 280C pierces the outer surface of anterior portion 292 of body 282.

Figure 15B:
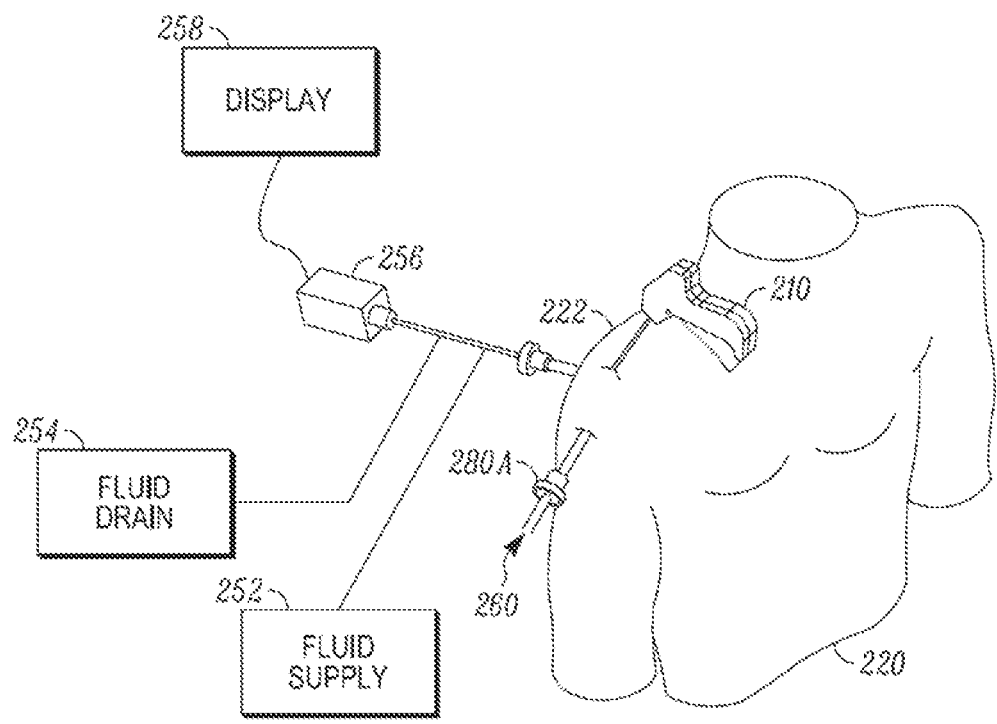
FIG. 15B is a stylized perspective view illustrating an exemplary procedure for arthroscopic treatment of a shoulder of a patient, according to an example of the present disclosure.

FIG. 15B is a stylized perspective view illustrating an exemplary procedure for treating a shoulder 222 of a patient 220 using implant device system 100. The procedure illustrated in FIG. 15B may include, for example, fixing tendon repair implants to one or more tendons of shoulder 222. The tendons treated may be torn, partially torn, have internal micro-tears, be untorn, and/or be thinned due to age, injury or overuse.

Shoulder 222 of FIG. 15B has been inflated to create a cavity therein. A fluid supply 252 is pumping a continuous flow of saline into the cavity. This flow of saline exits the cavity via a fluid drain 254. A camera 256 provides images from inside the cavity. The images provided by camera 256 may be viewed on a display 258. Camera 256 may be used to visually inspect the tendons of shoulder 222 for damage. An implant, such as implant 114 or sheet-like implant 250 may be affixed to a bursal surface of the tendon regardless of whether there are visible signs of tendon damage.

An implant delivery system 260 can be seen extending from shoulder 222 in FIG. 15B. In some examples, implant delivery system 260 may be similar to system 100, including implant delivery device 101, implant positioning device 112, implant 114, and sheath 103. Implant delivery system 260 is extending through first cannula 280A. In certain embodiments, first cannula 280A can access a treatment site within shoulder 222 using a lateral approach in which first cannula 280A pierces the outer surface of a right side of the patient's body. In some cases a physician may choose not to use a cannula in conjunction with implant delivery system 260. When that is the case, the implant delivery system 260 may be advanced through tissue. Implant delivery system 260 comprises a sheath that is affixed to a handle. The sheath defines a lumen and a distal opening fluidly communicating with the lumen. In the embodiment of FIG. 15B, the distal opening of the sheath has been placed in fluid communication with the cavity created in shoulder 222.

An implant, such as implant 114 or sheet-like implant 250 is at least partially disposed in the lumen defined by a sheath of implant delivery system 260, for example sheath 103. Implant delivery system 260 can be used to place the tendon repair implant inside shoulder 222. In some embodiments, the implant is folded into a compact configuration, in accordance with the above described techniques, when inside the lumen of the sheath. When this is the case, implant delivery system 260 may be used to unfold the implant into an expanded shape. Additionally, implant delivery system 260 can be used to hold the implant against the tendon.

The implant may be affixed to the tendon while it is held against the tendon by implant delivery system 260. Various attachment elements may be used to fix the implant to the tendon. Examples of attachment elements that may be suitable in some applications include sutures, tissue anchors, bone anchors, and staples. Various attachment elements may be used to fix implant 114 the implant site. Examples of attachment elements that may be suitable in some applications include sutures, tissue anchors, bone anchors, and staples. Details of exemplary tendon staples may be found in commonly assigned co-pending applications: U.S. application Ser. No. 12/684,774 filed Jan. 8, 2010; U.S. application Ser. No. 12/729,029 filed Mar. 22, 2010; U.S. application Ser. No. 12/794,540 filed Jun. 4, 2010; U.S. application Ser. No. 12/794,551 filed on Jun. 4, 2010; U.S. application Ser. No. 12/794,677 filed on Jun. 4, 2010; and U.S. Application No. 61/443,180 filed on Feb. 15, 2011, the disclosures of which are incorporated herein by reference. Exemplary bone staples are described in commonly assigned applications: U.S. Application No. 61/577,626 filed Dec. 19, 2011; U.S. Application No. 61/577,632 filed Dec. 19, 2011 and U.S. Application No. 61/577,635 filed Dec. 19, 2011, the disclosures of which are incorporated herein by reference. Exemplary staples in many of the above applications may be used for anchoring in both soft tissue and in bone.

In the exemplary embodiment of FIG. 15B, the shaft of a fixation tool 210 is shown extending into shoulder 222. In one exemplary embodiment, fixation tool 210 is capable of affixing the implant to the tendon and bone with one or more staples while the implant may be held against the tendon by implant delivery system 260.

Figure 16A:
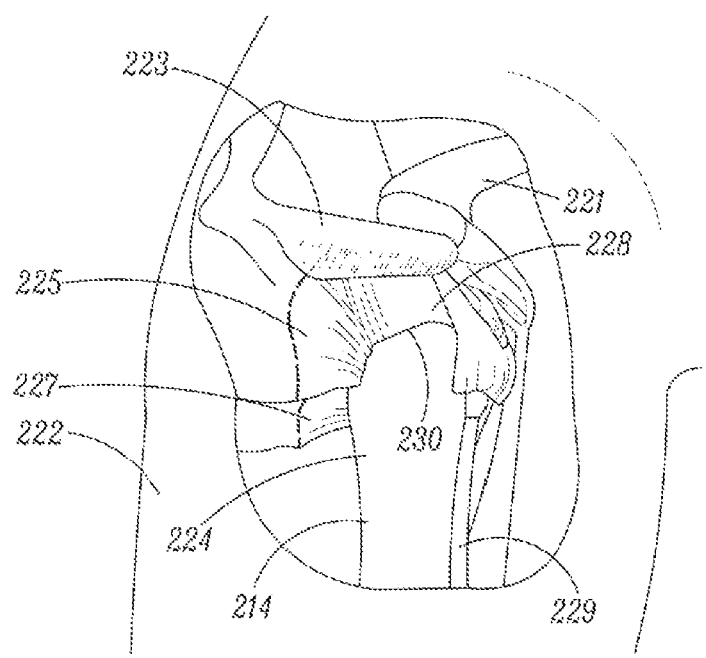
FIG. 16A is a perspective view of a portion of a shoulder with parts removed to illustrate the supraspinatus tendon in relation to other anatomical features, according to an example of the present disclosure.
Figure 16B:
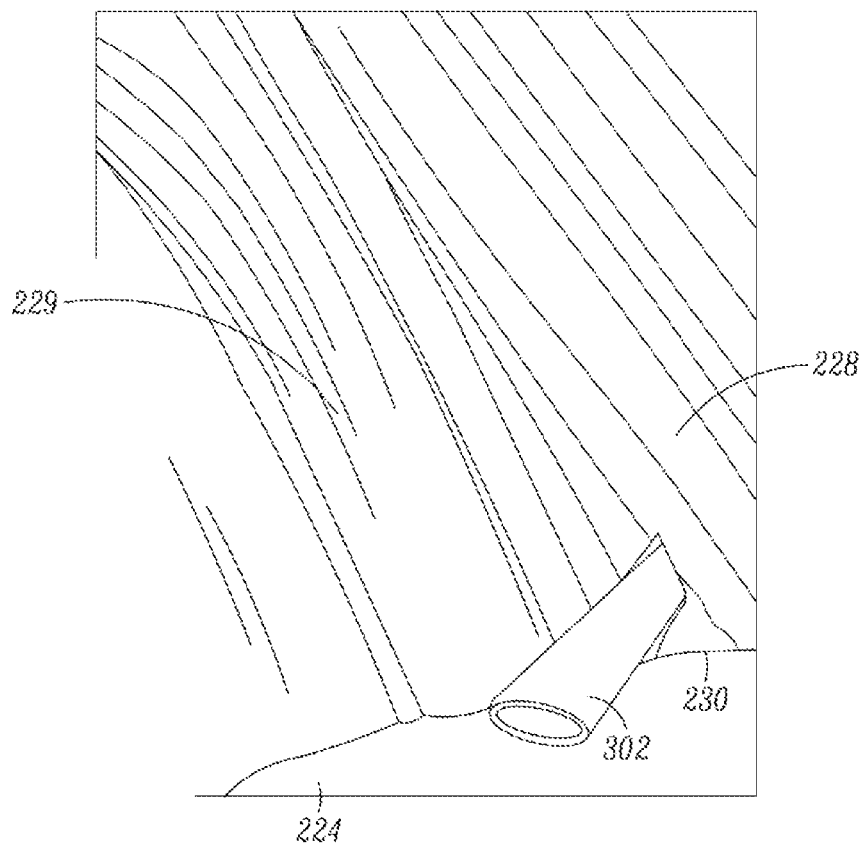
FIG. 16B is a partial perspective view of an articular side of the supraspinatus tendon illustrating the position relative to the biceps tendon and a marker inserted from the bursal side to identify the location of the biceps tendon which is not visible from the bursal side, according to an embodiment.
Figure 16C:
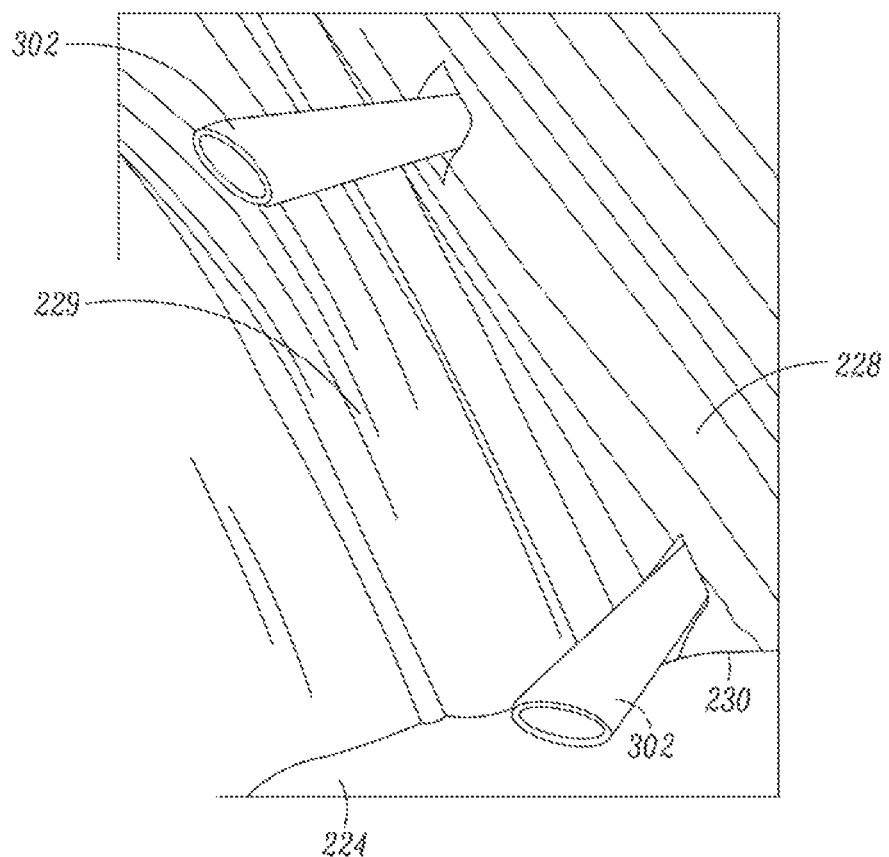
FIG. 16C is a partial perspective view of an articular side of the supraspinatus tendon with two markers inserted to delineate the biceps tendon over its length which is not visible from the bursal side, according to an example of the present disclosure.
Figure 16D:
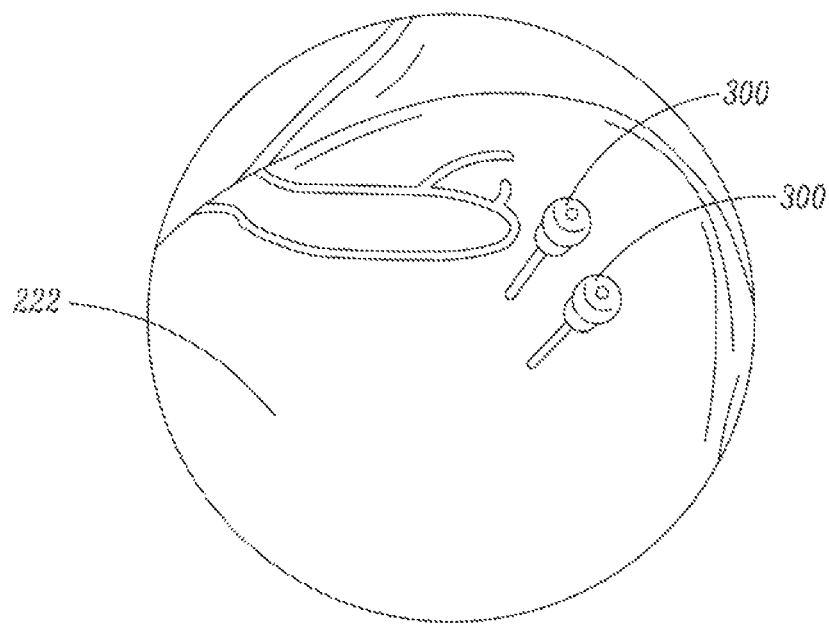
FIG. 16D is a partial perspective view of the shoulder showing two markers as they extend proximally from a point of insertion in the skin, according to an example of the present disclosure.
Figure 16E:
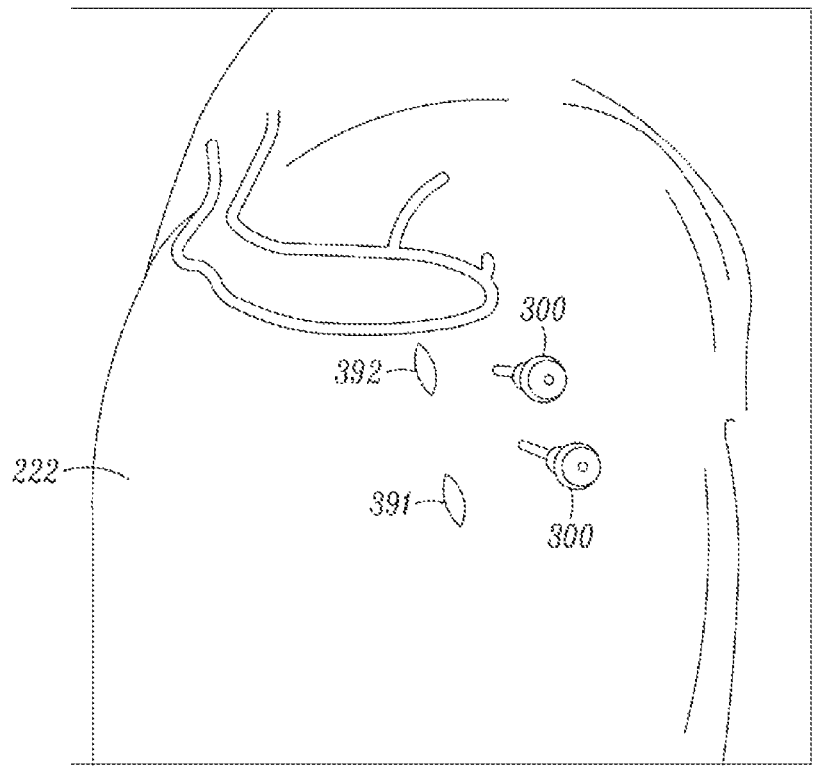
FIG. 16E is a partial perspective view of a shoulder with two portal incisions made relative to two markers according to an example of the present disclosure.
Figure 16F:
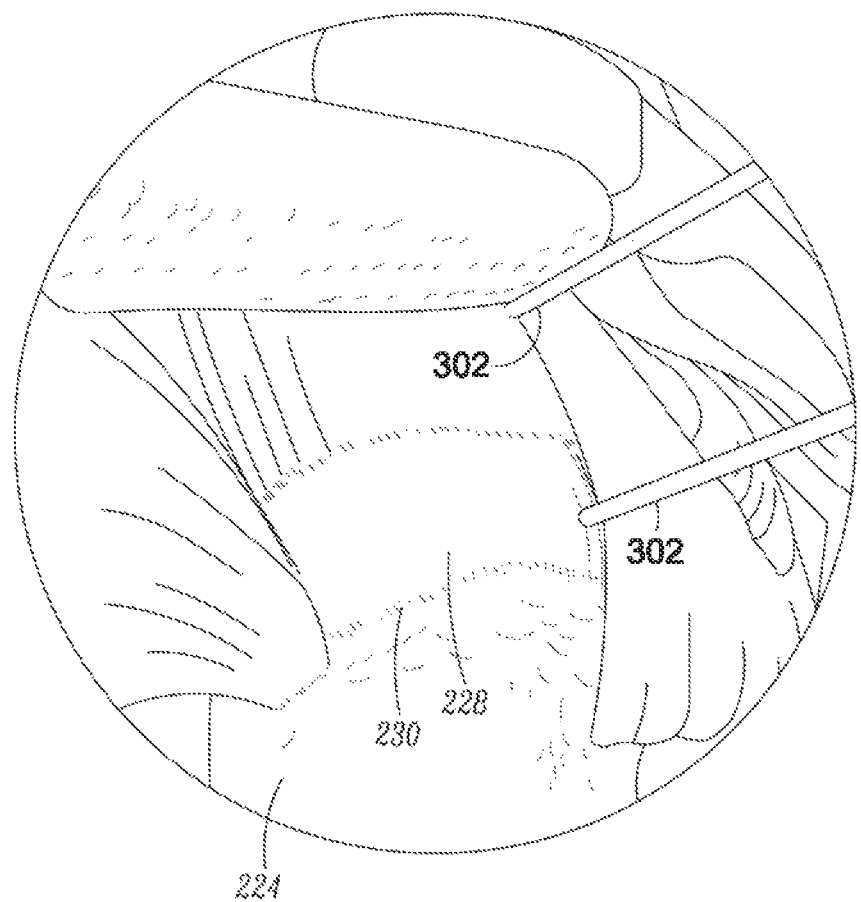
FIG. 16F is a partial perspective view of a shoulder depicting two markers from the bursal side of the tendon as they extend therethrough and would be seen during arthroscopic placement of an implant, according to an example of the present disclosure.
Figure 16G:
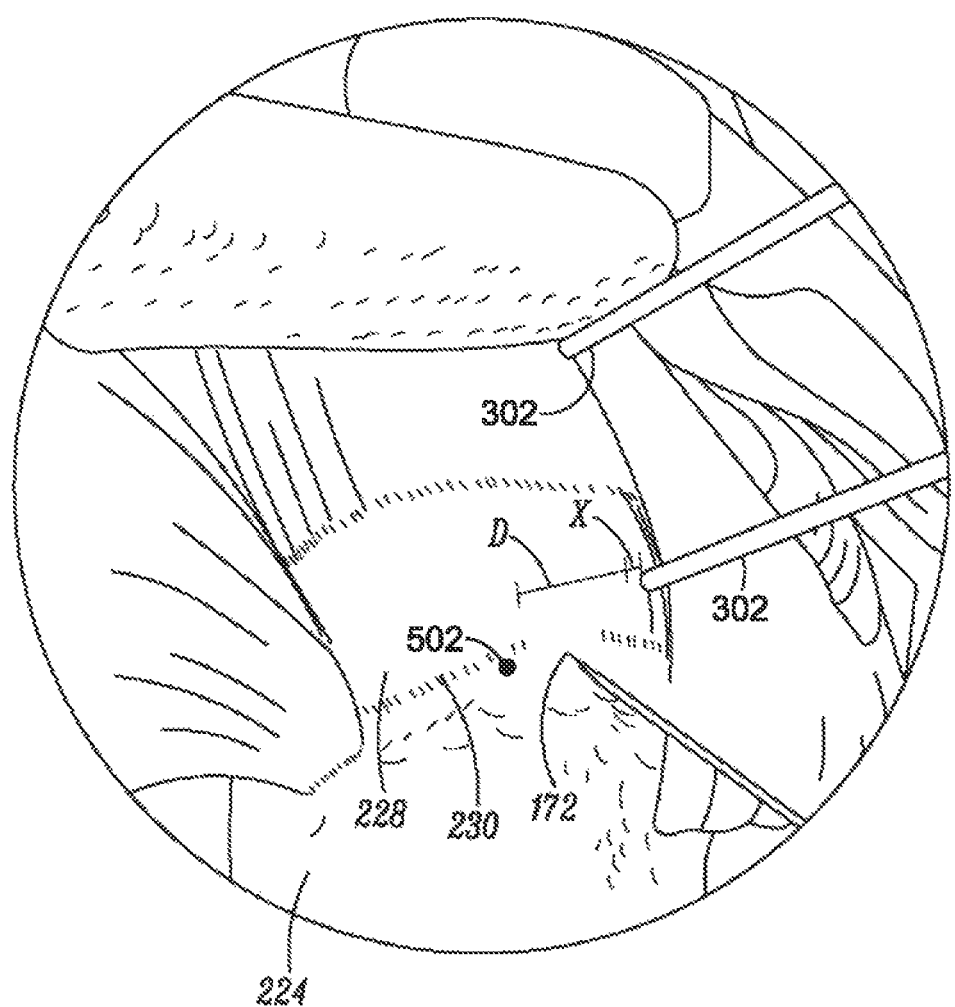
FIG. 16G is a partial perspective view of a shoulder illustrating placement of a guidewire relative to markers, according to an example of the present disclosure.
Figure 16H:
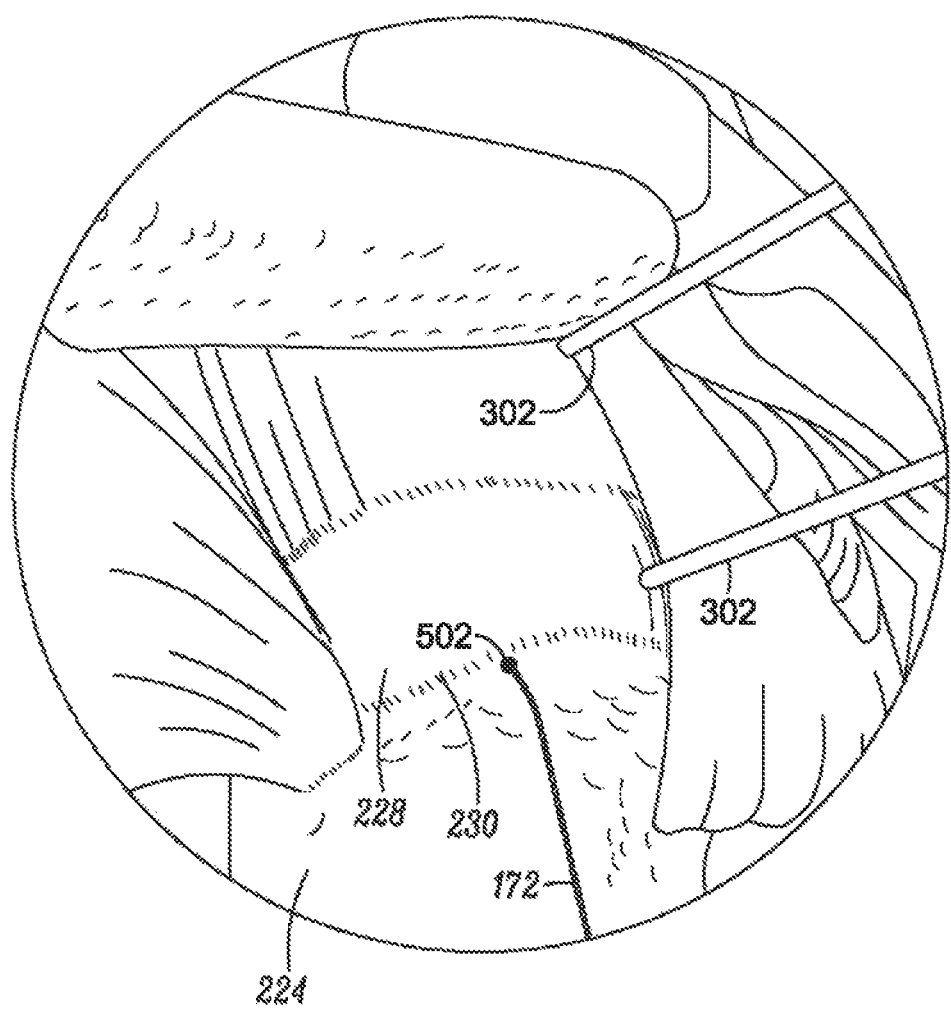
FIG. 16H is a partial perspective view illustrating a guidewire affixed to bone relative to markers, according to an example of the present disclosure.
Figure 16I:
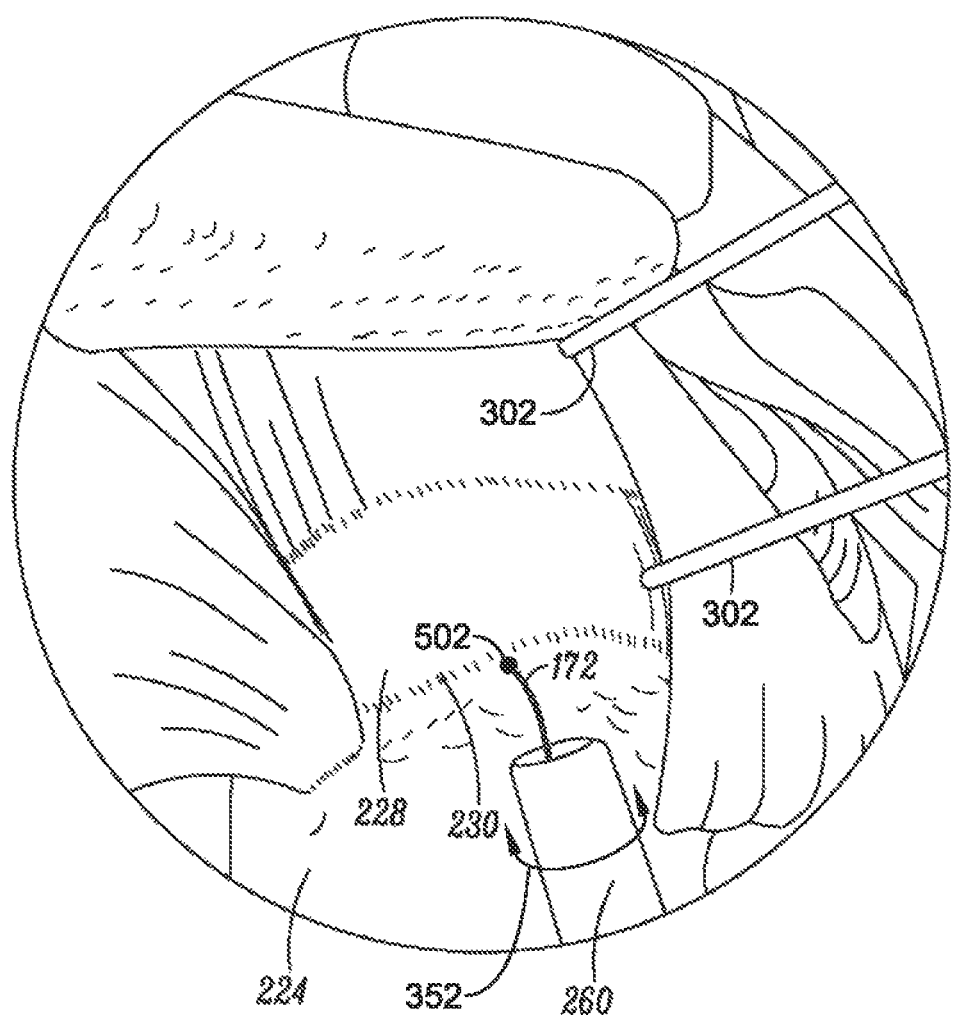
FIG. 16I is a partial perspective view of a shoulder with an implant delivery system guided over a guidewire, according to an example of the present disclosure.
Figure 16J:
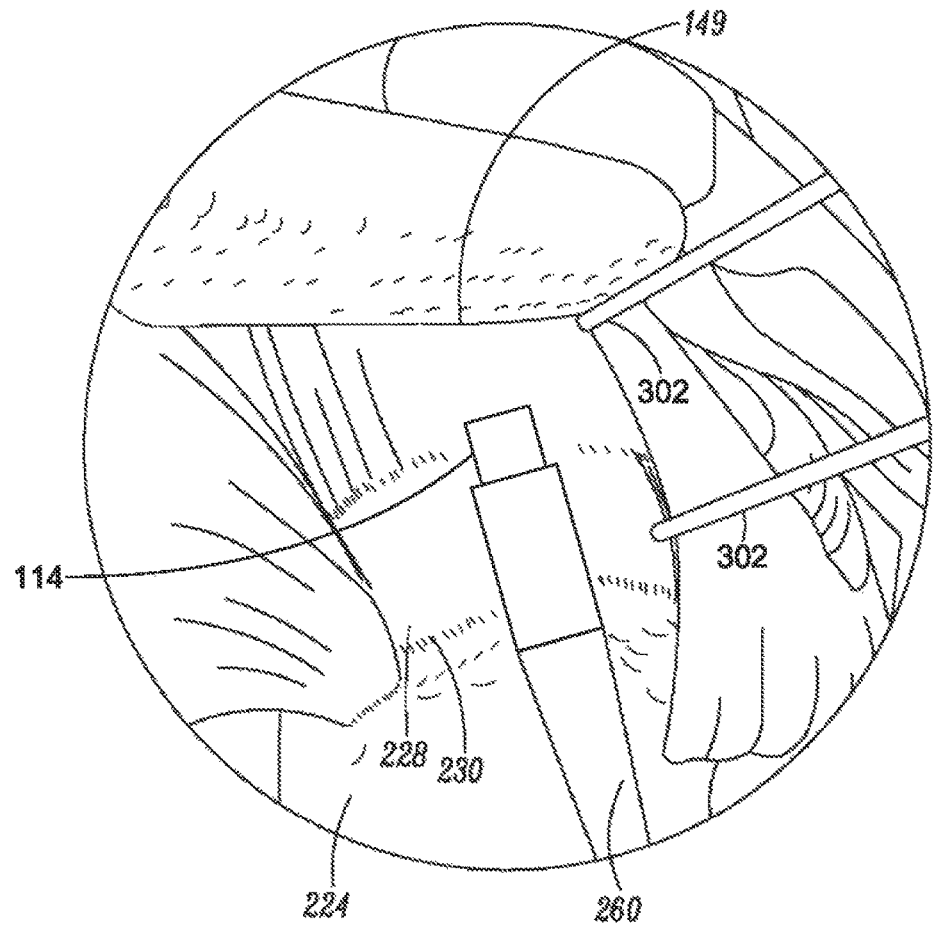
FIG. 16J is a partial perspective view of a shoulder illustrating a partial retraction of a sheath of an implant delivery system, according to an example of the present disclosure.
Figure 16K:
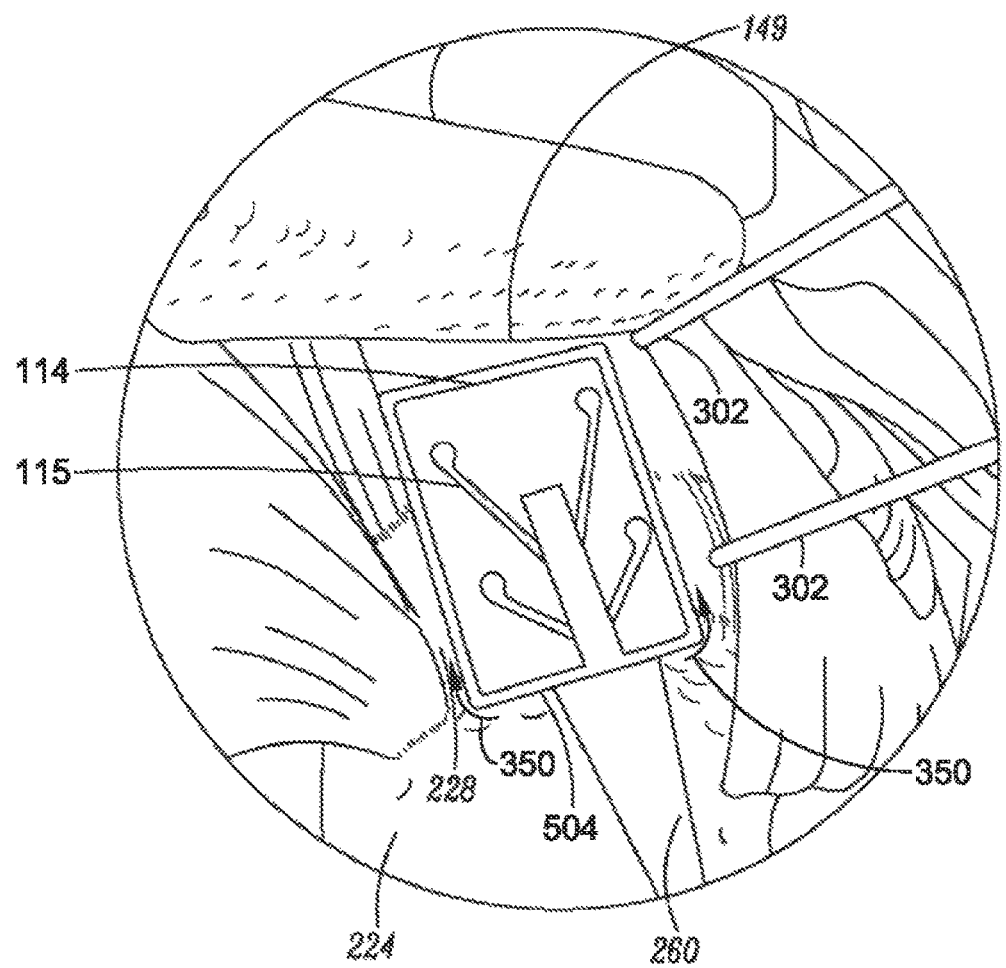
FIG. 16K is a partial perspective view of a shoulder illustrating a deployment and positioning of an implant relative to markers, according to an example of the present disclosure.
Figure 16L:
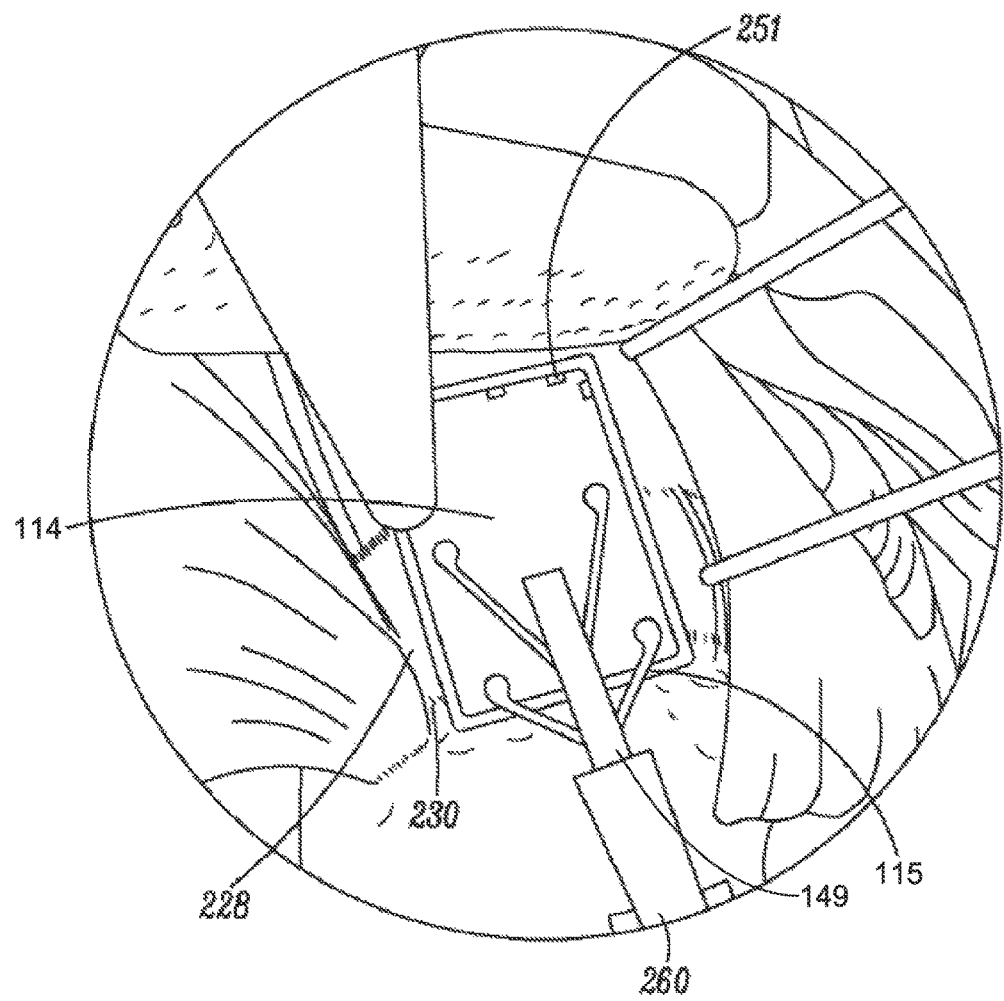
FIG. 16L is a partial perspective view of a shoulder depicting partial retraction of an implant delivery system as an implant is affixed by staples to a tendon, according to an example of the present disclosure.
Figure 16M:
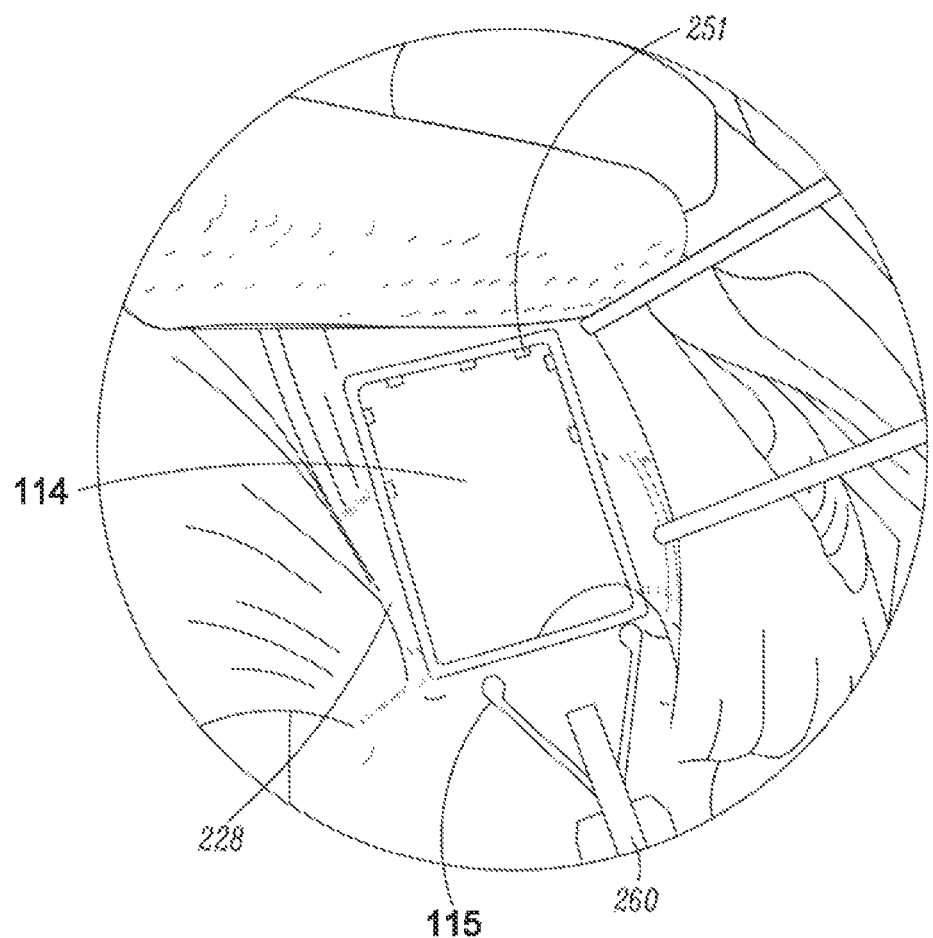
FIG. 16M is a partial perspective view of a shoulder depicting a retraction of an implant delivery system from a shoulder, according to an example of the present disclosure.
Figure 16N:
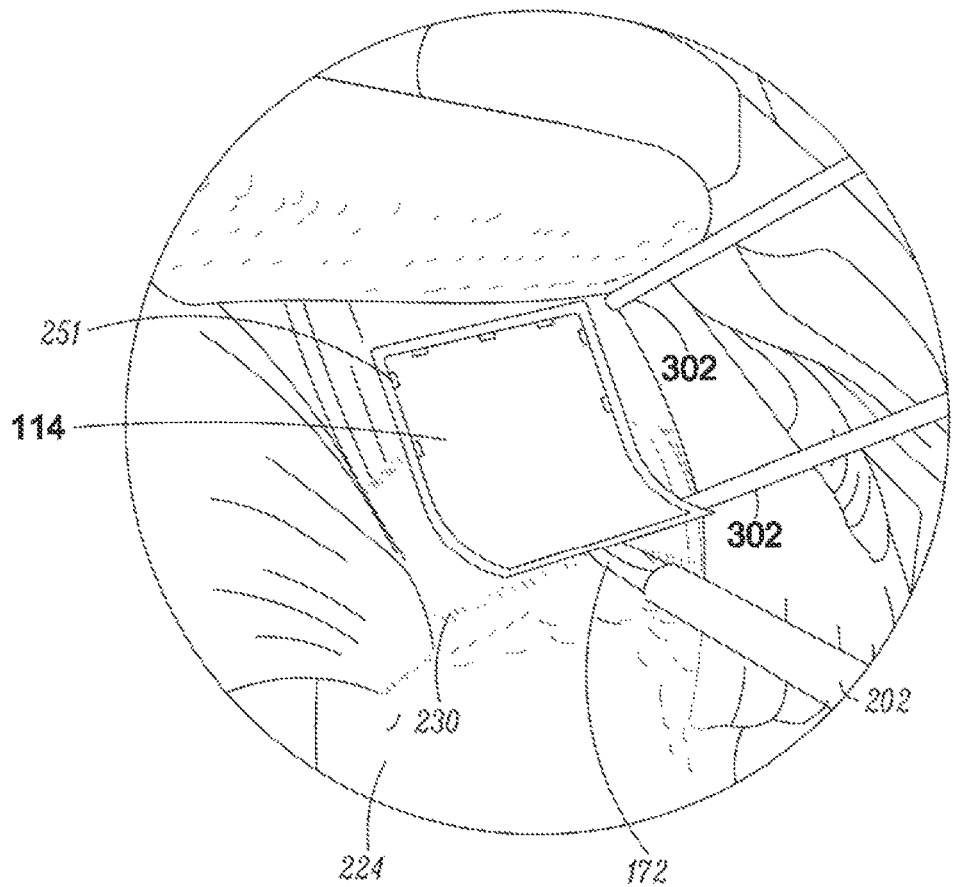
FIG. 16N is a partial perspective view of a shoulder depicting removal of a guidewire from the shoulder prior to affixing a proximal portion of an implant to the humeral head, according to an example of the present disclosure.

Referring to FIGS. 16A-16N, a series of step-wise illustrations are provided of exemplary use of markers, guidewire, and implant delivery system, such as system 100, as an overall kit for treatment of the supraspinatus tendon of the shoulder. The supraspinatus tendon is used to illustrate one use of the system, but the system may be used in other areas of the body. In particular, the system may be used in areas of the body requiring accurate placement of an implant relative to other anatomical structures as the system is guided to a marked first position by the guidewire and the system may be rotated about the guidewire to proper orientation relative to at least one, and at times two other markers of anatomical structure.

Referring now to FIG. 16A, shoulder 222 is schematically illustrated with skin and other obstructing tissue removed so that humerus 214 and supraspinatus tendon 228 are readily visible for purposes of better understanding exemplary procedures using the devices and methods of the current disclosure. Humerus 214 and supraspinatus tendon 228 are shown in relation to clavicle 221 and acromion 223. Further, infraspinatus tendon 225 and teres minor tendon 227 are shown as they attach to the humerus, and as previously stated, interdigitate with the supraspinatus. The point of insertion 230 of the supraspinatus tendon 228 to humeral head 224 is also indicated and generally forms a line. Biceps tendon 229 can be seen as it extends down the arm, however, this tendon is not visible from this bursal side view on the rotator cuff of the shoulder as biceps tendon 229 passes underneath the supraspinatus tendon and runs on the articular side of the supraspinatus tendon (beneath the tendon).

FIG. 16B illustrates a view of the articular side of supraspinatus tendon 228 near point of insertion 230 on humeral head 224. This view can be seen by a surgeon through the arthroscope when positioned beneath the supraspinatus tendon. As can be seen in the illustration, biceps tendon 229 is visible as it runs medially to the shoulder attachment. In treating the supraspinatus tendon with an implant over the bursal side of the tendon, it is preferred to not interfere with the biceps tendon by putting a staple or other attachment into this tendon. Therefore, as a first step in one example method, the location of the biceps tendon is marked so it is known when viewing the bursal side of the supraspinatus tendon. As illustrated in FIG. 16B, shaft 302 of a marker assembly 300 (shown in FIG. 16D) has been inserted through the skin of the shoulder and the bursal side of supraspinatus tendon 228 to project into the space depicted with the location being adjacent biceps tendon 229 proximate the point of insertion 230. In some example methods, a second marker system 300 is used to mark a second point medial of first marker. This is illustrated in FIG. 16C which shows a shaft 302 penetrating the bursal side of supraspinatus tendon 228 and adjacent biceps tendon 229 at a location medial to the first marker.

FIG. 16D shows the shoulder as it appears on the skin surface with the two marker systems 300 inserted. The two points of insertion define a line that runs parallel to the biceps tendon under the supraspinatus tendon which indicates an area where the implant should not be located or attached to avoid interfering with the biceps tendon. FIG. 16E shows two of three incision ports that can be made relative to the marker systems 300. A first port can be located on the posterior side of the shoulder for inserting the arthroscope (not shown). A second port, inferior lateral port 391, is made for insertion of the implant delivery system. A third port, superior lateral port 392, is made for insertion of devices that are used to attach the implant to the tendon and bone.

A view of the bursal side of supraspinatus tendon 228 with markers projecting therethrough is illustrated in FIG. 16F. The drawing indicates a clear visible line at the frontal margin of the supraspinatus tendon in line with the markers. Due to other tissue and ligaments in the area this is not visible to the surgeon through the arthroscope. Therefore, the markers, as placed while viewing the biceps tendon from the articular side delineate the front edge of where one would want to place the implant.

With the front edge location of the implant delineated, the next step in one method of the present disclosure is placement and attachment of a guidewire. As illustrated in FIG. 16G, with the width of the implant selected for the tendon known, a first fixed point 502 is located a distance D plus an additional distance X in the posterior direction from the line identified by the shafts 302. In some embodiments the distance D is one-half of the width of the implant plus a distance X of about 2 mm in the posterior direction from the line defined by the shafts 302. Further, the longitudinal distance between an implant mounted on the delivery system used and the guidewire port on the delivery shaft may be known. In the illustrated method, using one representative delivery system, it is known that the longitudinal location of first fixed point 502 should be at the insertion point. As the implant is delivered, it will then extend from the line defined by the point of insertion 230 down the arm of the patient about 5 mm, which assures the implant extends over the point of insertion and is affixed to the humeral head 24.

First fixed point 502 may be determined through observation and/or measurement of a treatment site or tissue to be covered by the implant relative to other anatomy. For example, in treating a rotator cuff injury, a physician can measure the supraspinatus tendon lateral width and observe the location of the line generally defining the point of insertion of the tendon into the humeral head. With these measurements known, along with the known size of implant to be used and the longitudinal/lateral location of the loaded implant relative to the guidewire port, a best location for first fixed point 502 can be selected and the guidewire fixed thereto.

Determining first fixed point 502 for the implant location, however, may not adequately position the implant as it can be rotated, at least to some degree, about first fixed point 502. Therefore, in some embodiments, at least a second anatomical point or position may be identified and/or marked to assure the implant is rotated to a proper position on first fixed point 502. In some embodiments a third anatomical point or position may also be identified and/or marked, in which embodiment the second and third point can define a line which is generally parallel to an edge of the implant when properly rotated about the first point. In treating the supraspinatus tendon, a marker can be placed through the skin and tendon while viewing the articular side of the supraspinatus tendon where the biceps tendon is also visible. The marker can be inserted adjacent the biceps tendon to delineate its location and assure the implant is rotated to generally parallel the biceps tendon and avoid any staples attaching to such tendon which may interfere with its function.

As illustrated in FIG. 16G, guidewire 172 may be placed at the identified first fixed point 502. In some examples, guidewire 172 may have a tissue retention member affixed to a distal end. The tissue retention member may provide a temporary connection of the distal end of the guidewire to the bone or other tissue. In some examples, the means for affixing can include a K-wire (Kirshner wire) which can be a smooth stainless steel pin with a drill tip that cuts into bone when rotated. Alternatively, the means for fixing can include a screw that is threaded or a fine pin that is hammered into bone or other tissue. The fine pin can include barbs or other projections and/or surface texture that aid in temporarily fixing the distal end of the guidewire to the bone or other tissue at first fixed point 502.

FIG. 16H illustrates guidewire 172 after attachment to humeral head 224 proximate point of insertion 230 and located posterior to the line defined by markers 308 by a distance of one-half the width of the implant to be delivered plus about 2 mm. Implant delivery system 260, such as implant delivery system 100 described above and include device 101, may then be tracked over the guidewire 172 into the vicinity of the implant site as depicted in FIG. 16I. For example, sheath 103 of system 260 may be slid over the proximal end of guidewire 172, e.g. the end not affixed to patient 220. Guidewire 103 may track groove 193 of implant device 112 as system 260 is advanced over guidewire 172. Next, guidewire 172 may pass through engagement head 108 and into inner tube 110. Once inside inner tube 110, system 260 may be advanced until the proximal end of guidewire 172 connects with stopper 135. Upon further advancement of guidewire 172, stopper 135 may apply a force to indicator 123 sufficient to overcome the biasing force of spring 137, causing indicator 123 to provide an indication, such as by extending proximally from device 101. Additionally, in some examples, sheath 103 may include sheath slit 159, which may allow for easier manipulation of guidewire 172 or system 260 while advancing system 260 along guidewire 172.

Delivery system 260 is urged distally so that sheath 103 is proximate the fixed point where the guidewire 172 is attached to the bone. As indicated in FIG. 16J, this assures the proximal edge of implant 114 extends a distance beyond point of insertion 230, in a direction travelling down the patient's arm, and can be affixed to the humeral head 224. In some embodiments the distance Y is about 5 mm beyond point of insertion 230 and assures implant 114 can be affixed to humeral head 224.

Once system 260 is in the desired distal position, for example as indicated by indicator 123, system 260 may additionally be rotated about guidewire 172. This may be seen in FIG. 16I by arrows 352. Once system 260 is in the correct location, distally and rotationally, the physician may begin to press trigger 105 or otherwise actuate outer tube 102 relative to inner tube 110. As described previously, pressing trigger 105 may cause outer tube 102 to retract proximally, which in turn causes sheath 103 to retract proximally. FIG. 16J depicts a state when trigger 105 has been partially pressed, thereby partially retracting sheath 103 and exposing a portion of implant 114.

Referring now to FIG. 16K, once trigger 105 has been pressed a threshold amount and sheath 103 retracted a threshold amount, system 260 transitions into the deployed state. For example, once sheath 103 has been retraced a threshold amount, the potential energy stored in the elastically deformed implant positioning component 115 is no longer restrained by sheath 103. Accordingly, implant positioning component 115 may release stored kinetic energy and attempt to return to its rest state. This release of potential energy may impart a force on implant 114. The force on implant 114 may cause implant 114 to unroll, unfold, unwrap, uncurl, or otherwise revert to a deployed state, and thus no longer be disposed around implant device 112. The force imparted by implant positioning component 115 may also hold implant 114 against tendon 228. Once positioned against tendon 228, implant 114 may again be rotated about the first fixed point 502 (guidewire attachment to the bone) and indicated by arrows 350 so that an edge 504 of implant 114 is generally parallel to the line defined by the two markers 308. As next shown in FIG. 16L, implant 114 can be attached in multiple locations to supraspinatus tendon 228 using staples 251 or other fasteners. Once the medial edge is attached, implant delivery system 260 can be partially retracted while being used to smooth and pull implant 114 down and make sure it lays flat against the tendon while more staples are inserted into the tendon. In FIG. 16M, implant delivery system 260 may then be removed from the treatment site. Referring to FIG. 16M, prior to attaching the rest of the implant 114, the guidewire 172 may be removed in this embodiment as it may be located under the edge of implant 114. For example, guidewire delivery shaft 202 may be placed over the guidewire to remove the guidewire, as shown in FIG. 16N. Once removed, additional staples can be inserted in the tendon and in the bone along with removal of the markers 308.

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed:

1. An implant assembly comprising:
a one-piece implant positioning component including a trunk and a plurality of flexible appendages extending away from the trunk,
wherein the one-piece implant positioning component includes an elastically deformed undeployed configuration and a deployed configuration,
wherein the plurality of flexible appendages includes a first opposed pair of flexible appendages extending away from a first attachment location positioned along the trunk to their respective free ends and a second opposed pair of flexible appendages extending away from a second attachment location positioned along the trunk to their respective free ends, and wherein the first attachment location is spaced a fixed distance away from the second attachment location along a length of the trunk;
a sheet-like implant at least partially disposed around the one-piece implant positioning component in the elastically deformed undeployed configuration with the plurality of flexible appendages engaged with a first face of the implant; and
a sheath disposed around the one-piece implant positioning component and the sheet-like implant,
wherein the plurality of flexible appendages in the elastically deformed undeployed configuration and the sheet-like implant are configured to fold within the sheath,
wherein the plurality of flexible appendages in the deployed configuration engage the first face on a convex side of the sheet-like implant.

2. The assembly of claim 1, wherein the sheath is retractably disposed around the one-piece implant positioning component and the sheet-like implant.

3. The assembly of claim 1, wherein the sheath is configured to releasably engage with a delivery device.

4. The assembly of claim 1, wherein the sheath further comprises an engagement head for engaging with a delivery device.

5. The assembly of claim 4, wherein the engagement head comprises one or more notches.

6. The assembly of claim 5, wherein the one or more notches are configured to releasably engage one or more engagement arms of the delivery device, and wherein each of the one or more engagement arms comprises a latch to engage at least one of the one or more notches.

7. The assembly of claim 4, wherein the sheath is coupled to an outer tube of the delivery device, and wherein the one-piece implant positioning component is coupled to an inner tube of the delivery device.

8. The assembly of claim 1, wherein the sheath further comprises a guide wire slit.

9. The assembly of claim 1, wherein in the deployed configuration, the one-piece implant positioning component extends from a central longitudinal axis of the implant assembly.

10. The assembly of claim 9, wherein during a transition from the elastically deformed undeployed configuration to the deployed configuration, the one-piece implant positioning component applies a force to the sheet-like implant.

11. The assembly of claim 1, wherein the one-piece implant positioning component comprises a flexible metal.

12. The assembly of claim 11, wherein when the sheath is disposed about the one-piece implant positioning component, the sheath biases the one-piece implant positioning component to the elastically deformed undeployed configuration.

13. The assembly of claim 1, wherein the one-piece implant positioning component and the sheet-like implant move relative to the sheath to transition from the elastically deformed undeployed configuration to the deployed configuration.

14. The assembly of claim 13, wherein the sheet-like implant is uncovered by the sheath in the deployed configuration.

15. The assembly of claim 1, wherein the implant assembly is configured to engage an implant assembly loading vessel and a loading tube.

16. The assembly of claim 15, wherein the loading tube is configured to retain the one-piece implant positioning component in the elastically deformed undeployed configuration.

17. The assembly of claim 15, wherein the loading tube comprises a one-piece implant positioning component engagement slot configured to receive the one-piece implant positioning component.

18. The assembly of claim 17, wherein the one-piece implant positioning component traverses the one-piece implant positioning component engagement slot and at least partially resides in the loading tube.

19. The assembly of claim 15, wherein the plurality of flexible appendages are at least partially disposed within the loading tube when the loading tube engages the one-piece implant positioning component.

20. The assembly of claim 19, wherein the implant assembly loading vessel includes a first hinged member and a second hinged member, wherein the first hinged member includes a first recess and wherein the second hinged member includes a second recess, and wherein the implant assembly and the loading tube are configured to engage with the first recess and the second recess of the implant assembly loading vessel, and the loading tube is configured to securely engage with the first recess and the second recess of the implant assembly loading vessel and the implant assembly is configured to releasably engage with the implant assembly loading vessel.

21. The assembly of claim 20, wherein:
the first recess includes a raised tab; and
the loading tube further includes a slot configured to engage with the raised tab to securely engage the loading tube with the loading vessel.

22. The assembly of claim 20, wherein the loading vessel comprises one or more sheath head engagement portions configured to engage the sheath.

23. An implant assembly comprising:
a one-piece implant positioning component including a trunk and a plurality of flexible appendages extending away from the trunk,
wherein the one-piece implant positioning component includes an undeployed state having an elastically deformed undeployed configuration and a deployed state having a deployed configuration,
wherein the plurality of flexible appendages includes a first opposed pair of flexible appendages extending away from a first attachment location positioned along the trunk to their respective free ends and a second opposed pair of flexible appendages extending away from a second attachment location positioned along the trunk to their respective free ends, and wherein the first attachment location is spaced a fixed distance away from the second attachment location along a length of the trunk;
a sheet-like implant at least partially disposed along the one-piece implant positioning component with the plurality of flexible appendages engaged with a convex face of the sheet-like implant in the deployed configuration; and
a sheath disposed around the one-piece implant positioning component and the sheet-like implant;
wherein the one-piece implant positioning component is configured to elastically deform within the sheath.

24. The implant assembly of claim 23, wherein the sheath is configured to engage a distal end of an outer shaft, and wherein the one-piece implant positioning component is configured to engage an inner shaft, and wherein at least a portion of the inner shaft extends within a lumen of the outer shaft.

25. The implant assembly of claim 24, wherein the outer shaft is configured to shift from a first position in which the sheath covers the sheet-like implant to a second position in which the sheet-like implant is free of the sheath.

26. The implant assembly of claim 25, wherein shifting the outer shaft from the first position to the second position permits the sheet-like implant to unfold.

27. The implant assembly of claim 23, wherein the plurality of flexible appendages engages a first face of the sheet-like implant.

28. The implant assembly of claim 23, wherein the plurality of flexible appendages include an opening extending therethrough.

29. The implant assembly of claim 23, wherein the one-piece implant positioning component is shaped to maximize surface contact with the sheet-like implant.

30. An implant assembly comprising:
a one-piece implant positioning component including a trunk and a plurality of flexible appendages extending away from the trunk,
wherein the one-piece implant positioning component includes an undeployed state having an elastically deformed configuration and a deployed state having a second configuration,
wherein the plurality of flexible appendages includes a first opposed pair of flexible appendages extending away from a first attachment location positioned along the trunk to their respective free ends and a second opposed pair of flexible appendages extending away from a second attachment location positioned along the trunk to their respective free ends, and wherein the first attachment location is spaced a fixed distance away from the second attachment location along a length of the trunk;
a sheet-like implant at least partially disposed along the one-piece implant positioning component; and
a sheath disposed around the one-piece implant positioning component and the sheet-like implant in the undeployed state;
wherein the one-piece implant positioning component is movable between the undeployed state in which the plurality of flexible appendages are elastically deformed within the sheath to the deployed state in which the one-piece implant positioning component and the sheet-like implant are located distal of the sheath with the plurality of flexible appendages engaging a convex face of the sheet-like implant in the deployed state.

* * * * *